United States Patent
Ohmiya et al.

(10) Patent No.: US 11,015,176 B2
(45) Date of Patent: May 25, 2021

(54) NUCLEIC ACID ENCODING A LUMINESCENT ENZYME PROTEIN

(71) Applicant: NATIONAL INSTITUTE OF ADVANCED INDUSTRIAL SCIENCE AND TECHNOLOGY, Tokyo (JP)

(72) Inventors: Yoshihiro Ohmiya, Tsukuba (JP); Yasuo Mitani, Tsukuba (JP); Rie Yasuno, Tsukuba (JP)

(73) Assignee: NATIONAL INSTITUTE OF ADVANCED INDUSTRIAL SCIENCE AND TECHNOLOGY, Tokyo (JP)

( * ) Notice: Subject to any disclaimer, the term of this patent is extended or adjusted under 35 U.S.C. 154(b) by 0 days.

(21) Appl. No.: 16/082,925

(22) PCT Filed: Mar. 9, 2017

(86) PCT No.: PCT/JP2017/009467
§ 371 (c)(1),
(2) Date: Sep. 6, 2018

(87) PCT Pub. No.: WO2017/155036
PCT Pub. Date: Sep. 14, 2017

(65) Prior Publication Data
US 2019/0093086 A1 Mar. 28, 2019

(30) Foreign Application Priority Data
Mar. 11, 2016 (JP) .............................. JP2016-048403

(51) Int. Cl.
C12N 9/02 (2006.01)
C12N 15/09 (2006.01)
C12N 5/10 (2006.01)
C09K 11/06 (2006.01)

(52) U.S. Cl.
CPC ............ *C12N 9/0069* (2013.01); *C09K 11/06* (2013.01); *C12N 5/10* (2013.01); *C12N 15/09* (2013.01); *C12Y 113/12* (2013.01); *C12Y 113/12007* (2013.01)

(58) Field of Classification Search
CPC ................................................ C12N 15/8212
USPC ....................................................... 435/320.1
See application file for complete search history.

(56) References Cited

U.S. PATENT DOCUMENTS

| 5,641,641 A | 6/1997 | Wood |
| 5,650,289 A | 7/1997 | Wood |
| 7,078,181 B2 | 7/2006 | Hawkins et al. |
| 7,572,629 B2 | 8/2009 | Ohmiya et al. |
| 2007/0105172 A1 | 5/2007 | Ohmiya et al. |
| 2009/0220960 A1 | 9/2009 | Ohmiya et al. |
| 2012/0117667 A1 | 5/2012 | Klaubert et al. |

FOREIGN PATENT DOCUMENTS

| JP | 2007-159567 A | 6/2007 |
| JP | 4385135 B2 | 12/2009 |
| JP | 4484429 B2 | 6/2010 |
| JP | 2014-500011 A | 1/2014 |

OTHER PUBLICATIONS

Shimomura et al., "Partial purification and properties of the Odontosyllis luminescence system", Journal of Cellular Physiology, 1963, 61 (3), pp. 275-292.*
De Wet et al, Firefly Luciferase Gene: Structure and Expression in Mammalian Cells. Molecular and Cellular Biology, Feb. 1987, p. 725-737.*
Inoue et al, 6-Propionyllumazines from the Marine Polychaete, Odontosyllis undecimdonta. Chemistry Letters 19(3), 367-368, 1990.*
Mitani et al., "Novel gene encoding a unique luciferase from the fireworm *Odontsyllis undecimdonta*," *Sci. Rep.*, 8(1): 12789 (2018).
European Patent Office, Extended European Search Report in European Patent Application No. 17763376.5 (dated Oct. 9, 2019).
Deheyn et al., "Internal and secreted bioluminescence of the marine polychaete *Odontosyllis phosphorea* (Syllidae)," *Invertebrate Biol.*, 128(1): 31-45 (2009).
Hall et al., "Engineered Luciferase Reporter from a Deep Sea Shrimp Utilizing a Novel Imidazopyrazinone Substrate," *ACS Chem. Biol.*, 7(11): 1848-1857 (2012).
Hastings, "Chemistries and colors of bioluminescent reactions: a review," *Gene*, 173(1): 5-11 (1996).
Ishiguro et al., "Secretome Analysis Using Transcriptomic Sequence Database of *Flammulina velutipes*," *Journal of the Japan Wood Research Society*, 56(6): 388-396 (2010).
Kishi et al., "Cypridina Bioluminescence I: Structure of *Cypridina* Luciferin," *Tetrahedron Lett.*, 7(29): 3427-3436 (1966).
Mieda et al., "Isolation study of luciferin from the marine fireworm of the genus, *Odontosyllis*" The Chemical Society of Japan Koen Yokoshu, 86(2): 1400, Abstract No. 1PA-007 (2006).
Nakajima, "cDNA Cloning and Characterization of a Secreted Luciferase from the Luminous Japanese Ostracod, *Cypridina noctiluca*," *Biosci. Biotechnol. Biochem.*, 68(3): 565-570 (2004).
Nakajima et al., "Multicolor luciferase assay system: one-step monitoring of multiple gene expressions with a single substrate," *Bio Techniques*, 38(6): 891-894 (2005).
Ohmiya et al., "Bioluminescence in the Limpet-Like Snail, *Latia neritoides*," *Bull. Chem. Soc. Jpn.*, 78(7): 1197-1205 (2005).
Shimomura et al., "Partial Purification and Properties of the *Odontosyllis* Luminescence System," *J. Cell Physiol.*, 61(3): 275-292 (1963).
Shimomura et al., "Structure of the Light-Emitting Moiety of Aequorin," *Biochem.*, 11(9): 1602-1608 (1972).

(Continued)

*Primary Examiner* — Sheridan Swope
(74) *Attorney, Agent, or Firm* — Leydig, Voit & Mayer, Ltd.

(57) ABSTRACT

The present invention provides a luminescent enzyme protein comprising the amino acid sequence represented by SEQ ID NO: 2, and a mutant enzyme thereof.

8 Claims, 4 Drawing Sheets
Specification includes a Sequence Listing.

(56) References Cited

OTHER PUBLICATIONS

Verhaegen et al., "Recombinant *Gaussia* Luciferase. Overexpression, Purification, and Analytical Application of a Bioluminescent Reporter for DNA Hybridization," *Anal. Chem.*, 74(17): 4378-4385 (2002).

Viviani et al., "Cloning and Molecular Characterization of the cDNA for the Brazilian Larval Click-beetle *Pyrearinus termitilluminans* Luciferase," *Photochem. Photobiol.*, 70(2): 254-260 (1999).

Yoshino et al., "Mass Spectrometry-Based Protein Identification by Correlation with Sequence Database," *J. Mass. Spectrom. Soc. Jpn.*, 52(3): 106-129 (2004).

Japanese Patent Office, International Search Report in International Patent Application No. PCT/JP2017/009467 (dated May 30, 2017).

\* cited by examiner

SEQUENCE LISTING

<160> NUMBER OF SEQ ID NOS: 12

<210> SEQ ID NO 1
<211> LENGTH: 1252
<212> TYPE: DNA
<213> ORGANISM: Odontosyllis undecimdonta

<400> SEQUENCE: 1

```
tgagtaacag tgctaacttc atcatcacaa gaagatactt ctcagcttgt attgaagatg    60
aagttagcac tgttactcag cattggatgt tgcctggttg ccgtgaactt tgctttaagg   120
gctactatca taagatgtct taggaaaact agaagttggt cagaaataga ttgtacacca   180
catcaggaca agctatatga agactttgac aggatctggg caggagatta cctgtcggta   240
tttgctgaat ggttagataa tcccatccct cgagagtggt ctgaggaaag actggccaca   300
tactgcatag agagggaatg tcacactaat caagctatgg ttgactatat gaatatacat   360
gggtatgccc cttttttgcat ggaaaggagt gttgaagact gggtgaatgc tagattctgg   420
```

| | |
|---|---|
| actagatgta aggttagaac tgaccgtagt ttagaactgg cacctgaaga atatgccacc | 480 |
| tactttttgtt ataaggtgtt tcgtgtacag gatcctaaaa tagcttgtcc ctcgatggat | 540 |
| gtgatccttt cacctaacaa actgactgta caacaaatga tgcagaataa ggaaataaga | 600 |
| ggagttgtag aggatagatc tgagcaatgg tgggttggac taatgagaga atatcgcat | 660 |
| ctgtctaagg acttgaatgg tgtgaaacaa ttccattatg gatggatcat aaacacagct | 720 |
| acacaaaaga atgtggttcc tttgtggtca cgttatcagg gcctactat tccagtaaga | 780 |
| agagacatgc ctagaatcat taatgccatg tctaatggag gaggaaacat caccttggga | 840 |
| gatattcgaa atttccactg ctcagctgat ccagacagtg ttgctgtcat ctgccctgag | 900 |
| tttggtttct tgtcctatag tccagctgaa actatagtta tggttccagt aaatggatta | 960 |
| atcctgatgg gaatgacaca atctgcagat ggagtaccct tcgtaaaatc tgcactattt | 1020 |
| gctgagatgt ataacctaca acagtaagag atcatccagg acactgaggc tgaatgtggt | 1080 |
| cattatttat acacagttta ttcccttaat ctttgcaaca ttataattta gttttgataa | 1140 |
| tcatgatgat taatgtagat ataatataaa catatattat atgatcagat actcttacta | 1200 |
| ttctttttat gctttgtttt tttattaaat tctccgcatt ttctattctg at | 1252 |

<210> SEQ ID NO 2
<211> LENGTH: 329
<212> TYPE: PRT
<213> ORGANISM: Odontosyllis undecimdonta

<400> SEQUENCE: 2

Met Lys Leu Ala Leu Leu Leu Ser Ile Gly Cys Cys Leu Val Ala Val
1               5                   10                  15

Asn Phe Ala Leu Arg Ala Thr Ile Ile Arg Cys Leu Arg Lys Thr Arg
            20                  25                  30

Ser Trp Ser Glu Ile Asp Cys Thr Pro His Gln Asp Lys Leu Tyr Glu
        35                  40                  45

Asp Phe Asp Arg Ile Trp Ala Gly Asp Tyr Leu Ser Val Phe Ala Glu
    50                  55                  60

Trp Leu Asp Asn Pro Ile Pro Arg Glu Trp Ser Glu Glu Arg Leu Ala
65                  70                  75                  80

Thr Tyr Cys Ile Glu Arg Glu Cys His Thr Asn Gln Ala Met Val Asp
                85                  90                  95

Tyr Met Asn Ile His Gly Tyr Ala Pro Phe Cys Met Glu Arg Ser Val
            100                 105                 110

Glu Asp Trp Val Asn Ala Arg Phe Trp Thr Arg Cys Lys Val Arg Thr
        115                 120                 125

Asp Arg Ser Leu Glu Leu Ala Pro Glu Glu Tyr Ala Thr Tyr Phe Cys
    130                 135                 140

Tyr Lys Val Phe Arg Val Gln Asp Pro Lys Ile Ala Cys Pro Ser Met
145                 150                 155                 160

Asp Val Ile Leu Ser Pro Asn Lys Leu Thr Val Gln Gln Met Met Gln
                165                 170                 175

Asn Lys Glu Ile Arg Gly Val Val Glu Asp Arg Ser Glu Gln Trp Trp
            180                 185                 190

Val Gly Leu Met Arg Glu Ile Ser His Leu Ser Lys Asp Leu Asn Gly
        195                 200                 205

Val Lys Gln Phe His Tyr Gly Trp Ile Ile Asn Thr Ala Thr Gln Lys
    210                 215                 220

Asn Val Val Pro Leu Trp Ser Arg Tyr Gln Gly Pro Thr Ile Pro Val

```
                225                 230                 235                 240
Arg Arg Asp Met Pro Arg Ile Ile Asn Ala Met Ser Asn Gly Gly Gly
                    245                 250                 255

Asn Ile Thr Leu Gly Asp Ile Arg Asn Phe His Cys Ser Pro Asp Pro
                260                 265                 270

Asp Ser Val Ala Val Ile Cys Pro Glu Phe Gly Phe Leu Ser Tyr Ser
            275                 280                 285

Pro Ala Glu Thr Ile Val Met Val Pro Val Asn Gly Leu Ile Leu Met
        290                 295                 300

Gly Met Thr Gln Ser Thr Asp Gly Val Pro Phe Val Lys Ser Ala Leu
305                 310                 315                 320

Phe Ala Glu Met Tyr Asn Leu Gln Gln
                325

<210> SEQ ID NO 3
<211> LENGTH: 27
<212> TYPE: DNA
<213> ORGANISM: Artificial sequence
<220> FEATURE:
<223> OTHER INFORMATION: PCR primer

<400> SEQUENCE: 3
catatgaagt tagcactgtt actcagc                                      27

<210> SEQ ID NO 4
<211> LENGTH: 30
<212> TYPE: DNA
<213> ORGANISM: Artificial sequence
<220> FEATURE:
<223> OTHER INFORMATION: PCR primer

<400> SEQUENCE: 4
tctagactgt tgtaggttat acatctcagc                                   30

<210> SEQ ID NO 5
<211> LENGTH: 4805
<212> TYPE: DNA
<213> ORGANISM: Odontosyllis undecimdonta

<400> SEQUENCE: 5
atgaagttag cactgttact cagcattgga tgttgcctgg ttgccgtcaa ctttgcttta    60
agggctacta tcataagatg tcttagggta agacttcaga aactcatatt gaccatgagg   120
gcctctataa taatatttct taatgtaaga ctacagaagc tcatattgac cttaagggtc   180
tctataataa tatttcttaa tgtaagacta cagaagctca tattgacctt gagtctctat   240
aataatattt cttaatgtaa gacaacagaa gctcatattg accttgaggg tctctataat   300
aatacatata attcatctt gatttaatta tttctcttag aaaactagaa gttggtcaga   360
aatagattgt acaccacatc aggacaagct atatgaggac tttgacagga tctgggctgg   420
agattacctg tcagtatttg ccgaatggtt agataatccc atccctcgag agtggtctga   480
ggaaagactg gccacatact gcatagagag ggaatgtcac actaatcaag ctatggtgga   540
ctatatgaat atacatgggg taaagtttta gcacatgttt ttatgtacag atctgctttt   600
attatggttt taatcgtagt acattttata tgtatagtat ctgctttatt atggttttaa   660
tcttagtaca tgtttatatt tacagtatgc cccttataat ggttttaatc ttggtacatg   720
tttgtactta cagtatctgc tttattatgg ttttaatctt agtacatgtt tgtatttaca   780
gtatctgcct tattatggtt ttaatcttag tacatgtttt gtacttacag tatgcccctt   840
```

```
tttgcatgga aaggagtgtt gaagactggg tgaatgctag attctggact aggtatgcag      900
tttcatcaaa tgtttatatc aataaaatat aatgcttagt aaagcagctg ccaatccggg      960
ttaagtattt ttttccaag cacatttgta caaaacggca tagtatccat agtgtaggga      1020
caattctttg gaatggtcaa ttctacactg cagtcagtga ttgatagtta taaatatgtc     1080
agattcagca attaatggtt aatgaatgaa ttgctattta ccacaatgtt gtaccattac     1140
aacattcagc taggctgtcc agccatcaaa cacatactca gtgtgctcct tctacatatt     1200
tgtactgatc tgcactacat ggaagttttt tctagactag tggtgcatgt attgcatatg     1260
actgtacttt agttctagga aaggagagtg ttaactacac ccttgagtag ttataggcaa     1320
caaacatgaa gttacctttt caattgaacc atgttgacag tgggctgtat acagctcgga     1380
agtagcctaa gcagggtaaa agtagccaat aaatcatatt gtggcaaaca gcaattcctt     1440
ttgcctcata ataattaat gatggatatt ccaaaaagtg tctagggag agtgagagac       1500 tttttgaag aaattgtatg gttttagata acagtcatac tatatacaaa tagttgcagc      1560
caaatctctt cctttcttca agataatttg tttcttcatc atttactaca ttcccaaatt     1620
gttctgtggc aagttgaaaa taggaaaaac atcctacaaa ttggattctg attcctcata     1680
acctaaggca aactcatctc cttgattcag aatgtagcaa taatctaccc atattcccca    1740
tgtaatttgt ttcattgacc ttcaaatcaa atgctctgtt attcctcctc attatcaata    1800
atatgattac ttttgcagat gtaaggttag aactgatcgt agtttagaac tggcacctga    1860
agaatatgcc acctactttt gttataaggt gtttcgtgta caggatccta aaatagcttg     1920
tccctcgatg gatgtgatcc tttcacctaa caaactgact gtacaacaaa tgatgcaaaa     1980
taaggtaaga accaccccta agccaggcca tacttatttg atagttcaga ctcatgtgca     2040
ggaaggagtg ccctgtgaca tactgcatat attttgaacc aaaatatttg tatacttgta    2100
gttaaaatca atgtgagcga cacttttagat aagagccaat ggttcattag atagtccaaa   2160
tcaatgtgag cgagacttta gagaagagcc aatggttcgg tagatagtcc aaatcaatct    2220
gagctagact ttagagaaga gcaatggttc attagatagt tcaaatcaat atgagctaga    2280
ctttagagaa gagccaatgg ttcggtagat agtccaaatc aatctgcgct agactttaga    2340
gaagagcaat ggttcattag atagtccaaa tcaatatgtt tctagacttt agagaagagc    2400
caatggttca ttagatagtt caaatcaata tgagctagac tttagagaag agccaatggt    2460
tcattagata gttcaaatca atatgagcta gactttagag aagagcaatg gttcagtaga    2520
tagttcaaat caatatgagc tagactttag agaagagcca atacaatatg agctagactt    2580
tagagaaggc caagtggtat aaggtgcaat taatctcaat aaaagagtca aacctttgag    2640
aagatagctt gaatcttaag aaggaaggca tcttaataga agatccacaa gattgtttaa    2700
attaagggag acacagctaa acgaaaaagc caagaaggct aatgaagcgg tactgacatt    2760
tttacttgtt tataccacag gaaataagag gagttgtaga ggatagatct gagcaatggt    2820
gggttggact aatgagagaa atatcgcatc tgtctaagga cttgaatggt gtgaaacaat    2880
tccattatgg atggatcata aacacagcta cacaaaagaa tgtggttcct ttgtggtcac    2940
gttatcaggg ggtaagaaat tctacattat aagaatgtga tttattaagc ttgctcatca    3000
ctttgtgttg gcacattgta tttgctactg ctagatcctt gagtgaactt aactcatata    3060
acttagaatc tgcatgcata ttttcaacta gacatagtaa taatatttta cataaatcac    3120
ttccttgcat aacagaaaat gttctgaatt ttgtattaaa cagtccttaa ctctggaccc    3180
```

| | |
|---|---|
| tctaaacatt aaaaatactg ttggacccta agtccatttt aaagtgagct aagtcaagtc | 3240 |
| ccactgttat agcaatttta aatttaaatg aagcctccag tcaagattgc aaaaagtctc | 3300 |
| agaaggatac agatttgtga tcccctcta aaatttgtaa ataacaaaat gaatagatct | 3360 |
| tgacatagcc atacatattt gcatatgact atccaaaggt ttttggagag ataatttt | 3420 |
| tctcctccca ttaggaggtg tttttgaggt aaccaaaata ttaccccccc tccccatgga | 3480 |
| tatggatgag gggtatactt ttctttcata tttcaatcta aaaatcccctt tttccaactt | 3540 |
| aaacaatttg aacttagttt acactaagtc aactaattta gtatcccatc ctttaccta | 3600 |
| cttgtagtct gaaactgtgt ggtattagga agaatcacag tttaaatgta catgagctat | 3660 |
| tttagcccaa tacaaactaa tgatattttt ttcagcccta ctattccagt aagaagagac | 3720 |
| atgcctagaa tcattaatgc catgtctaat ggaggaggaa acattacctt gggaggtaaa | 3780 |
| taaataaata aaaacttgta taaacataaa tattgcatca ctgaagcaaa taaacctatc | 3840 |
| tacctgctga agctgctaaa ctggatattc actgaacatt tgtaatatt ggtttattat | 3900 |
| tatgttgatg ggattcaaat aataataaaa tttacaaata tatgttctgt aaaattggca | 3960 |
| gccagccagg aaaaacgata aaatatagat gtatattgta ttgttgtcac ttttatcca | 4020 |
| atttagagac caggatgaaa catttagtca ataataaaca tatatatata gttattttat | 4080 |
| taaatctcaa gctacaatta taagtgctgg taaatagttg atcaataacc attttcatg | 4140 |
| aaataaataa aataaaatga tcagtaaaat ctcaatacat catcataact acagataaat | 4200 |
| tattttgtag atattcgaaa tttccactgc tctcctgatc cagacagtgt tgctgtcatc | 4260 |
| tgccctgagt tcggttttctt gtcctatagc ccagctgaaa ctatagtaat ggttccagta | 4320 |
| aatggatgta agattgcatt tccttattat ctaaataata attatgtaga gtactacttc | 4380 |
| cccttcaag ctgtttatcc agtctttgtt atctcatatt caatattctg tgtaataagt | 4440 |
| ttaaccctca agaatagaaa tgtaagcctg caggtgtagt aatgacctcc tgtaggtgta | 4500 |
| gtaatggcct cctgtaacca gtagtattaa tcgtataaag tatactattg tcattacaac | 4560 |
| acatctagaa ctgtggaggc caaaagtgga aattgtaaaa ccatccacaa taaactggtg | 4620 |
| ctatataaaa acgtagagta aagggatgtac aattcttaaa gtatcaaaca atgcaccaa | 4680 |
| cacaccatca ctattgccat aactatattt ctatttcagt aatcctgatg ggaatgacac | 4740 |
| aatctacaga tggagtacct ttcgtaaaat ctgccctatt tgctgagatg tataacctac | 4800 |
| aacag | 4805 |

<210> SEQ ID NO 6
<211> LENGTH: 29
<212> TYPE: DNA
<213> ORGANISM: Artificial sequence
<220> FEATURE:
<223> OTHER INFORMATION: PCR primer

<400> SEQUENCE: 6
acaagcttat gaagttagca ctgttactc                                    29

<210> SEQ ID NO 7
<211> LENGTH: 29
<212> TYPE: DNA
<213> ORGANISM: Artificial sequence
<220> FEATURE:
<223> OTHER INFORMATION: PCR primer

<400> SEQUENCE: 7
aacccgggtt actgttgtag gttatacat                                    29

<210> SEQ ID NO 8
<211> LENGTH: 21
<212> TYPE: DNA
<213> ORGANISM: Artificial sequence
<220> FEATURE:
<223> OTHER INFORMATION: PCR primer

<400> SEQUENCE: 8
atgaagttag cactgttact c                                            21

<210> SEQ ID NO 9
<211> LENGTH: 21
<212> TYPE: DNA
<213> ORGANISM: Artificial sequence
<220> FEATURE:
<223> OTHER INFORMATION: PCR primer

<400> SEQUENCE: 9
ggtagatcaa ttctgacggt t                                            21

<210> SEQ ID NO 10
<211> LENGTH: 987
<212> TYPE: DNA
<213> ORGANISM: Odontosyllis undecimdonta

<400> SEQUENCE: 10
atgaagttag cactgttact cagcattgga tgttgcctgg ttgccgtcaa ctttgcttta    60
agggctacta tcataagatg tcttaggaaa actagaagtt ggtcagaaat agattgtaca   120
ccacatcagg acaagctata tgaggacttt gacaggatct gggctggaga ttacctgtca   180
gtatttgccg aatggttaga taatcccatc cctcgagagt ggtctgagga agactggcc    240 acatactgca tagagaggga atgtcacact aatcaagcta tggtggacta tatgaatata   300
catgggtatg cccctttttg catggaaagg agtgttgaag actgggtgaa tgctagattc   360
tggactaggt gtaaggttag aactgatcgt agtttagaac tggcacctga agaatatgcc   420
acctactttt gttataaggt gtttcgtgta caggatccta aaatagcttg tccctcgatg   480
gatgtgatcc tttcacctaa caaactgact gtacaacaaa tgatgcaaaa taggaaata   540 agaggagttg tagaggatag atctgagcaa tggtgggttg gactaatgag agaaatatcg   600
catctgtcta aggacttgaa tggtgtgaaa caattccatt atggatggat cataaacaca   660
gctacacaaa agaatgtggt tccttttgtgg tcacgttatc aggggcctac tattccagta   720
agaagagaca tgcctagaat cattaatgcc atgtctaatg gaggaggaaa cattaccttg   780
ggagatattc gaaattcca ctgctctcct gatccagaca gtgttgctgt catctgccct    840
gagttcggtt tcttgtccta tagcccagct gaaactatag taatggttcc agtaaatgga   900
ttaatcctga tgggaatgac acaatctaca gatggagtac ctttcgtaaa atctgcccta   960
tttgctgaga tgtataacct acaacag                                      987

<210> SEQ ID NO 11
<211> LENGTH: 8
<212> TYPE: PRT
<213> ORGANISM: Artificial sequence
<220> FEATURE:
<223> OTHER INFORMATION: Synthetic Sequence - MS-MS result

<400> SEQUENCE: 11

Trp Glu Asp Trp Val Asn Ala Arg
1               5

```
<210> SEQ ID NO 12
<211> LENGTH: 8
<212> TYPE: PRT
<213> ORGANISM: Artificial sequence
<220> FEATURE:
<223> OTHER INFORMATION: Synthetic Sequence - MS/MS result

<400> SEQUENCE: 12

Trp Glu Asp Trp Val Asn Ala Arg
1               5
```

NUCLEIC ACID ENCODING A LUMINESCENT ENZYME PROTEIN

CROSS-REFERENCE TO RELATED APPLICATIONS

This patent application is the U.S. national phase of International Patent Application No. PCT/JP2017/009467, filed Mar. 9, 2017, which claims the benefit of Japanese Patent Application No. 2016-048403, filed on Mar. 11, 2016, which are incorporated by reference in their entireties herein.

INCORPORATION-BY-REFERENCE OF MATERIAL ELECTRONICALLY SUBMITTED

Incorporated by reference in its entirety herein is a computer-readable nucleotide/amino acid sequence listing submitted concurrently herewith and identified as follows: 17,834 bytes ASCII (Text) file named "740397Replacement-SequenceListing.txt," created Apr. 7, 2020.

TECHNICAL FIELD

The present invention relates to a luminescent enzyme protein (luminescent protein, luminescent enzyme, luciferase).

BACKGROUND ART

A luminescent enzyme (luciferase) is a general name for an enzyme that oxidizes a luminescent substrate (luciferin) and thereby produces luminescence during the oxidation process. Four types of bioluminescence involving a luminescent enzyme and luminescent substrate are known: a luciferin-luciferase type (LL-type), a photoprotein type, an intermolecular energy transfer type, and an intramolecular energy transfer type (Non-Patent Document 1).

In LL-type luminescence, a luminescent substrate and a luminescent enzyme are reacted, and the substrate serves as a light-emitter. In photoprotein-type luminescence, a luminescent substrate inherently present in a luminescent apoenzyme forms a complex, and is activated, for example, by an increase in calcium ion concentration as a trigger, thereby serving as a light-emitter. In the intermolecular energy transfer luminescence, which is based on the LL-type or photoprotein-type, the produced light excites a luminescent protein in the vicinity of the luminescent enzyme-substrate complex and thereby causes a luminescence shifted to a longer wavelength side. In intramolecular energy transfer luminescence, the energy generated by a reaction of a luminescent substrate and a luminescent enzyme excites an emitter, which is different from the substrate inherently present in the luminescent enzyme, and thereby causes luminescence.

The LL-type is the simplest reaction form, and therefore is suitable for reporter assay systems, bioimaging, or the like. Some commercial luminescent products derived from fireflies, *Cypridina*, click beatle (*Pynearinus termitilluminans*), railroad worms, and the like, have already been available and used. For example, a single reporter assay system using a firefly luminescence system (Patent Documents 1 and 2), a dual reporter assay system using a combination of a firefly luminescence system and a *Renilla* luminescence system (Patent Document 3), a highly luminescent reporter assay system using a low-molecular-weight luminescent enzyme of an *Oplophorus gracilirostris* luminescence system (Patent Document 4 and Non-Patent Document 2), and the like, have been sold by Promega KK. A high throughput reporter assay system using a *Cypridina* secreted luminescence system has been sold by ATTO (Non-Patent Document 3 and Patent Document 5). Luciferase assay systems using secreted luminescence systems of copepod *Gaussia* and *Cypridina* have been sold by New England BioLab (Non-Patent Document 4). A simultaneous three-color reporter assay system using a single luminescent enzyme obtained by modifying an *Iriomote* firefly (Japanese railroad worm) luminescence system and a railroad worm luminescence system (Non-Patent Document 5, and Patent Documents 6 and 7) and a high safety and high strength reporter assay system using a *Pynearinus termitilluminans* luminescence system (Non-Patent Document 6) have been sold by Toyobo Co., Ltd.

All of these products use LL-type reaction bioluminescence. Among coleopterans, firefly luciferin has been used as a common luminescent substrate; among *Cypridina*, *Cypridina* luciferin has been used as a luminescent substrate; and among both *Gaussia* and *Renilla*, coelenterazine has been used as a luminescent substrate. *Cypridina* luciferin and coelenterazine are different molecules; however, they both have an imidazopyrazinone structure as the main skeleton (Non-Patent Documents 7 and 8). Furimazine, which has been newly produced as a luminescent substrate, is used as a luminescent substrate of the *Oplophorus gracilirostris*-derived luminescent enzyme from Promega KK, which is also a molecule having an imidazopyrazinone structure.

A multi-reporter assay system is implemented by combining multiple luminescence systems with different wavelengths. However, at present, the usable wavelength range is 530 to 630 nm for firefly luciferin systems, and is 460 to 490 nm for *Cypridina luciferin* and coelenterazine systems. Generally, many pelagic luminescent organisms have a maximum luminescence wavelength of 450 to 490, and many land-dwelling organisms have a maximum luminescence wavelength of 550 to 580. In contrast, luminescence near 500 nm can be found in coastal luminescent organisms (Non-Patent Document 9) although infrequently. However, there have been no examples of gene cloning of a luminescence system near 500 nm, therefore; this luminescence system has not been practically used in a reporter assay system or the like. In particular, the wavelength of 510 nm, which corresponds to the middle of 490 nm and 530 nm that have been used so far, is highly usable in the combined use of other luminescence systems.

CITATION LIST

Patent Documents

Patent Document 1: U.S. Pat. No. 5,641,641
Patent Document 2: U.S. Pat. No. 5,650,289
Patent Document 3: U.S. Pat. No. 7,078,181
Patent Document 4: JP2014-500011A
Patent Document 5: Japanese Patent No. 4484429
Patent Document 6: Japanese Patent No. 4385135
Patent Document 7: U.S. Pat. No. 7,572,629
Patent Document 8: JP2007-159567A

Non-Patent Documents

Non-Patent Document 1: Ohmiya et al., Bioluminescence in the Limpet-like snail, *Latia neritoides*, Bull. Chem. Soc. Jpn, 78, 1197-1205, 2005

Non-Patent Document 2: Hall et al., Engineered luciferase reporter from a deep sea shrimp utilizing a novel imidazopyrazinone substrate, ACS Chem. Biol, 7, 1848-1857, 2012

Non-Patent Document 3: Nakajima et al., cDNA cloning and characterization of a secreted luciferase from the luminous Japanese Ostracod, *Cypridina noctiluca*, Biosci. Biotechnol. Biochem., 68, 565-570, 2004

Non-Patent Document 4: Verhaegent and Christopoulos, Recombinant *Gaussia* luciferase. Overexpression, purification, and analytical application of a bioluminescent reporter for DNA hybridization, Anal. Chem., 74, 4378-4385, 2002

Non-Patent Document 5: Nakajima et al., Multicolor luciferase assay system: one-step monitoring of multiple gene expression with a single substrate, Biotechniques, 38, 891-894, 2005

Non-Patent Document 6: Viviani et al., Cloning and molecular characterization of the cDNA for the Brazilian larval click-beetle *Pyrearinus termitilluminans* luciferase, Photochem. Photobiol., 70, 254-260, 1999

Non-Patent Document 7: Kishi et al., *Cypridina* bioluminescence I: structure of *Cypridina* luciferin, Tetrahedron Lett., 7, 3427-3436, 1966

Non-Patent Document 8: Shimomura and Johnson, Structure of the light-emitting moiety of aequorin, Biochemistry, 11, 1602-1608, 1972

Non-Patent Document 9: Hastings, Chemistries and colors of bioluminescent reactions: a review, Gene, 173, 5-11, 1996

SUMMARY OF INVENTION

Technical Problem

An object of the present invention is to provide a novel luminescent enzyme protein.

The bioluminescence systems widely used by a person skilled in the art are as detailed above; only limited ranges of luminescence wavelength can be obtained by the luminescent substrates, luminescent enzymes and their genes, or luminescent reactions. In particular, luminescence systems with a wavelength near the maximum luminescence wavelength of 510 nm including those modified in luminescence characteristics, such as the luminescence spectrum, by modifying the enzyme, substrate, and the like, have not been specified. Therefore, developments of a novel luminescent enzyme in the wavelength range and bioluminescence systems using the luminescent substrates thereof have been desired.

Solution to Problem

The inventors of the present invention carried out extensive research to solve the above problems; as a result, the inventors found that a luminescent enzyme protein originated from *Odontosyllis undecimdonta* (a lugworm of the family syllidae) has a luminescence color near 510 nm, and various important properties in practical use, such as stability, luminescence strength, and the like. The present invention was completed by further study based on the above finding.

The present invention encompasses the following embodiments.

Item 1. A luminescent enzyme protein of any of the following:

(i) a luminescent enzyme protein comprising the amino acid sequence represented by SEQ ID NO: 2;

(ii) a luminescent enzyme protein comprising the amino acid sequence represented by SEQ ID NO: 2 in which one or more amino acid residues are substituted, added, or deleted, and having luciferase activity;

(iii) a luminescent enzyme protein comprising an amino acid having an identity of not less than 70% with the amino acid sequence represented by SEQ ID NO: 2;

(iv) a luminescent enzyme protein comprising an amino acid sequence encoded by the base sequence represented by SEQ ID NO: 10;

(v) a luminescent enzyme protein comprising an amino acid sequence encoded by the base sequence represented by SEQ ID NO: 10 in which one or more bases are substituted, added, or deleted, and having luciferase activity;

(vi) a luminescent enzyme protein comprising an amino acid sequence encoded by a base sequence having an identity of not less than 70% with the base sequence represented by SEQ ID NO: 10; and (vii) a luminescent enzyme protein comprising an amino acid sequence encoded by a base sequence that hybridizes with a nucleic acid consisting of a base sequence complementary to the base sequence represented by SEQ ID NO: 10 under a stringent condition, and having luciferase activity.

Item 1-1. A luminescent enzyme protein of any of the following:

(ii) a luminescent enzyme protein comprising the amino acid sequence represented by SEQ ID NO: 2 in which one or more amino acid residues are substituted, added, or deleted, and having luciferase activity;

(iii) a luminescent enzyme protein comprising an amino acid having an identity of not less than 70% and less than 100% with the amino acid sequence represented by SEQ ID NO: 2;

(v) a luminescent enzyme protein comprising an amino acid sequence encoded by the base sequence represented by SEQ ID NO: 10 in which one or more bases are substituted, added, or deleted, and also having luciferase activity;

(vi) a luminescent enzyme protein comprising an amino acid sequence encoded by a base sequence having an identity of not less than 70% and less than 100% with the base sequence represented by SEQ ID NO: 10; and (vii) a luminescent enzyme protein comprising an amino acid sequence encoded by a base sequence that hybridizes with a nucleic acid consisting of a base sequence complementary to the base sequence represented by SEQ ID NO: 10 under a stringent condition, and also having luciferase activity.

Item 2. The luminescent enzyme protein according to Item 1 or 1-1, wherein the luminescent enzyme protein has a luminescence wavelength of 490 to 530 nm at the peak intensity.

Item 3. A nucleic acid encoding the luminescent enzyme protein according to Item 1, 1-1, or 2.

Item 3-1. The nucleic acid according to Item 3, wherein the nucleic acid is an intron-free cDNA.

Item 4. A gene construct comprising a nucleic acid encoding the luminescent enzyme protein according to Item 1 or 2.

Item 4-1. The gene construct according to Item 4, wherein the nucleic acid is an intron-free cDNA.

Item 5. A cell in which the gene construct according to Item 4 or 4-1 is introduced.

Advantageous Effects of Invention

The present invention provides a novel luminescent enzyme protein. A preferred embodiment of the present invention provides a luminescent enzyme protein having a luminescence wavelength of the peak intensity between 490 nm and 530 nm used thus far, in particular, near 510 nm, which could not be achieved by a previously-known luminescent enzyme. With this luminescent enzyme protein alone, a new luminescence system can be constituted; further, a simultaneous multiple luminescence system can also be constituted by combining this protein with other luminescence systems.

DESCRIPTION OF EMBODIMENTS

Figure 1:
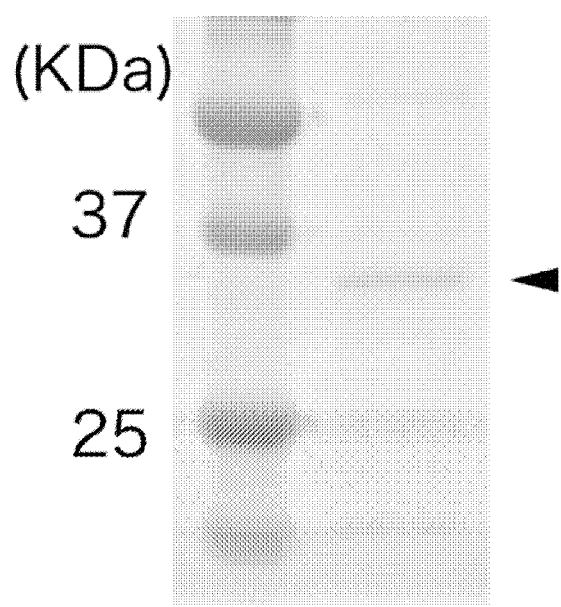
FIG. 1 shows SDS-PAGE analysis results with respect to a luminescent fluid of luminescent lugworm *Odontosyllis undecimdonta*.

The luminescent enzyme protein (which may hereinafter be simply referred to as a "luminescent enzyme") of the present invention encompasses the following embodiments.
(i) a luminescent enzyme protein comprising the amino acid sequence represented by SEQ ID NO: 2;
(ii) a luminescent enzyme protein comprising the amino acid sequence represented by SEQ ID NO: 2 in which one or more amino acid residues are substituted, added, or deleted, and also having luminescent enzyme activity;
(iii) a luminescent enzyme protein comprising an amino acid having a homology or identity of not less than 70% with the amino acid sequence represented by SEQ ID NO: 2;
(iv) a luminescent enzyme protein comprising an amino acid sequence encoded by the base sequence represented by SEQ ID NO: 10;
(v) a luminescent enzyme protein comprising an amino acid sequence encoded by the base sequence represented by SEQ ID NO: 10 in which one or more bases are substituted, added, or deleted, and also having luciferase activity;
(vi) a luminescent enzyme protein comprising an amino acid sequence encoded by a base sequence having an identity of not less than 70% with the base sequence represented by SEQ ID NO: 10; and
(vii) a luminescent enzyme protein comprising an amino acid sequence encoded by a base sequence that hybridizes with a nucleic acid consisting of a base sequence complementary to the base sequence represented by SEQ ID NO: 10 under a stringent condition, and also having luminescent enzyme activity.

In this specification, the expressions "comprising an amino acid sequence" and "comprising a base sequence" encompass an embodiment in which a part of the whole length of the amino acid sequence or the base sequence comprises the amino acid sequence or the base sequence, as well as an embodiment in which the whole length of the amino acid sequence or the base sequence essentially consists of the amino acid sequence or the base sequence (including an embodiment in which the whole length of the amino acid sequence or the base sequence consists only of the amino acid sequence or the base sequence).

The luminescent enzyme activity in the present invention refers to an enzymatic reaction activity by a luminescent enzyme and a substrate, and is measurable by detecting light (a luminescence spectrum) emitted from a substrate when the substrate is changed into the ground state after being excited by an enzymatic reaction with the luminescent enzyme. The light emitted upon the change into the ground state is detectable by using a known luminometer (e.g., AB-2350 PHELIOS; ATTO Corporation, or KARAFUL-LUC analyzer; Toyobo Co., Ltd.) or a spectrophotometer (e.g., AB-1850 LumiFL-Spectrocapture; ATTO Corporation).

In Item (ii), the number of the one or more amino-acid residues to be substituted, added, or deleted is not particularly limited insofar as it is an integer of 1 or larger. For example, the number of the amino-acid residues may be about 1 to several tens, preferably about 1 to 15, more preferably about 1 to 10, further preferably about 1 to 5, and particularly preferably about 1, 2, 3 or 4. Since this embodiment is an amino acid sequence resulting from substitution, addition or deletion of one or more amino acid residues with respect to the amino acid sequence represented by SEQ ID NO: 2, the embodiment does not include a protein having the amino acid sequence represented by SEQ ID NO: 2.

In an embodiment, the number of the one or more amino-acid residues to be substituted, added, or deleted is about 1 to 98 so that the identity of the amino acid sequence with the amino acid sequence represented by SEQ ID NO: 2 is 70% or more, preferably about 1 to 65 so that the identity is 80% or more, more preferably about 1 to 32 so that the identity is 90% or more, further preferably about 1 to 16 so that the identity is 95% or more, and particularly preferably about 1 to 6 or about 1 to 3 so that the identity is 98% or more or 99% or more.

The homology or identity of the amino acid sequence may be 70% or more, preferably 80% or more, more preferably 90% or more, further preferably 95% or more, and particularly preferably 984 or more or 99% or more. The homology or identity of the amino acid sequence may be less than 100%. The homology or identity of amino acid sequences may be determined by using a known algorithm, such as BLAST.

In Item (v), the number of the one or more bases to be substituted, added, or deleted is not particularly limited insofar as it is an integer of 1 or larger. For example, the number of the bases may be about 1 to several tens, preferably about 1 to 30, more preferably about 1 to 15, further preferably about 1 to 10, and particularly preferably about 1 to 5.

In an embodiment, the number of the one or more bases to be substituted, added, or deleted is about 1 to 296 so that the identity of the amino acid sequence with the base sequence represented by SEQ ID NO: 10 is 70% or more, preferably about 1 to 197 so that the identity is 80% or more, more preferably about 1 to 98 so that the identity is 90% or more, further preferably about 1 to 49 so that the identity is 95% or more, and particularly preferably about 1 to 19 or about 1 to 9 so that the identity is 98% or more or 99% or more.

In Item (vi), the homology or identity of the base sequence may be 70% or more, preferably 80% or more, more preferably 90% or more, further preferably 95% or more, and particularly preferably 98% or more or 99% or more. The homology or identity of the base sequences may be less than 100%. The homology or identity of the base sequences may be determined by using a known algorithm, such as BLAST.

In (vii), the "stringent condition" refers to a condition in which only a specific hybridization occurs and a non-specific hybridization does not occur. Examples of such a stringent condition of the present invention include, but are not limited to, a condition in which "hybridization is performed in 1×SSC (0.9M NaCl, 0.09M trisodium citrate) or 6×SSPE (3M NaCl, 0.2M $NaH_2PO_4$, 20 mM EDTA-2Na, pH7.4) at 42° C., followed by washing with 0.5×SSC at 42° C.".

The luminescent enzyme protein of the present invention may comprise a naturally occurring amino acid sequence or a modified naturally occurring amino acid sequence. In one embodiment of the present invention, the luminescent enzyme is a non-natural enzyme (an enzyme other than a natural enzyme).

When the luminescent enzyme of the present invention has a naturally occurring amino acid sequence, one preferable embodiment of the present invention is a luminescent enzyme originated from an *Odontosyllis undecimdonta*, a lugworm of the Family syllidae, encoded by the amino acid sequence represented by SEQ ID NO: 2 (329 amino acid residues) and the base sequence represented by SEQ ID NO: 10 (987 bases). The present invention also includes a homology of the luminescent enzyme originated from a lugworm of the Family syllidae other than *Odontosyllis undecimdonta* (in particular, a lugworm belonging to the genus *Odontosyllis* of the family Syllidae), encoded by the amino acid sequence represented by SEQ ID NO: 2 or the base sequence represented by SEQ ID NO: 10.

The homology of a luminescent enzyme may be originated from Alciopidae, Tomopteridae, Syllidae, Nereidae, Chaetopteridae, Cirratulidae, or Terebellidae. Examples of luminescent lugworm of the family Syllidae include *Odontosyllis phosphorea* from California, *Odontosyllis enopla* from the Caribbean Sea, and *Odontosyllis undecimdonta* from Toyama.

The luminescent enzyme protein of the present invention is not limited to a naturally occurring luminescent enzyme, and may be a luminescent enzyme obtained by modifying the amino acid sequence of a naturally occurring luminescent enzyme (which may hereinafter be simply referred to as "a mutant enzyme"). The modification form is not limited insofar as the luminescent enzyme has luciferase activity.

Examples of the modification form include, but are not limited to, the following.

Examples include a modification into an amino acid sequence for the purpose of changing the luminescence characteristics of the enzyme, such as the luminescence spectrum (e.g., maximal absorption wavelength) or luminescence intensity into a form different from that of a natural type.

Further, modification examples also include a modification of base sequence for the purpose of improving the translation efficiency and increasing the expression amount of the luminescent enzyme in the expression cells, such as (a) modification of the base sequence so as to avoid a bond of an undesired transcription factor, and (b) modification of a codon usage (uneven frequency in codon use) of a natural type (i.e., Syllidae lugworm) into a codon usage of a desired organism (e.g., mammals such as humans, or bacteria such as *Escherichia coli*). Examples also include modification of a restriction enzyme cleavage site in a base sequence that may limit the use.

The luminescent enzyme of the present invention also includes a fusion protein in which a second protein, a signal sequence, a tag sequence or the like is bonded to the N terminus or the C terminus of a naturally occurring amino acid sequence or a modification thereof. Further, the luminescent enzyme may be a luminescent enzyme consisting of an amino acid sequence obtained by deleting a part or the whole of a signal sequence in a naturally occurring amino acid sequence.

Examples of the second protein include the luminescent enzyme of the present invention, other luminescent proteins, such as a luciferase or a fluorescent protein, and maltose-binding proteins.

Examples of a signal sequence include protein-destabilizing signals, such as a PEST sequence, ubiquitin, or their biologically-active fragments, or their variants or derivatives; intracellular localization signals, such as a nuclear localization signal, membrane localization signal, cytoplasm localization signal, mitochondria localization signal, or ER localization signal. Further, examples among *Escherichia coli* or the like include a periplasm secretion signal.

Examples of a tag sequence include His-tag sequence, FLAG-tag sequence, and Avi-tag sequence.

In a preferred embodiment, the luminescence wavelength at the peak (maximum) intensity of the luminescent enzyme of the present invention is about 490 to 530 nm, preferably about 500 to 520 nm, more preferably about 505 to 515 nm, and particularly preferably about 510 nm. A luminescent enzyme having such a maximum (peak) wavelength has not previously been known. The luminescent enzyme may be combined with a known luminescent enzyme to construct a multicolor luminescence system.

The substrate (luminescent substrate) to be combined with the luminescent enzyme of the present invention may be a naturally occurring substrate or an artificially-synthesized substrate. To obtain a naturally occurring luminescent substrate, as described in the Examples, a luminescent lugworm (e.g., *Odontosyllis undecimdonta*) is disrupted in an organic solvent (e.g., alcohol, such as methanol, ethanol, or butanol) at a suitable temperature, or in a buffer solution having a high temperature sufficient to deactivate the luminescent enzyme inherent in a luminescent lugworm, followed by separation of the disruption residues from the supernatant by centrifugation or the like, thereby obtaining a crude liquid extract containing a luminescent substrate in the supernatant. When the substrate is artificially synthesized, the substrate may be produced by an organic synthesis method.

The luminescent enzyme protein of the present invention may be a naturally occurring luminescent enzyme protein or an artificially-produced luminescent enzyme protein.

To obtain a naturally occurring luminescent enzyme, as described in the Examples, a luminescent lugworm (e.g., *Odontosyllis undecimdonta*) is disrupted in a suitable buffer solution, followed by separation of the disruption residues from the supernatant by centrifugation or the like, thereby obtaining a crude liquid extract containing a luminescent enzyme in the supernatant. Since the crude liquid extract also contains a luminescent substrate, when the crude liquid extract is, for example, used for a luminescence assay, it is preferable to store the liquid extract as required until the luminescent substrate contained therein is consumed substantially completely by a luminescent reaction.

The naturally occurring luminescent enzyme may be obtained by partial purification or purification of the disrupted liquid extract, as necessary.

The artificially produced luminescent enzyme may be obtained by producing a recombinant enzyme by intracellular synthesis, followed by purification. More specifically, the artificially produced luminescent enzyme may be obtained according to a method similar to the method for producing a wild-type luciferase disclosed in JP2006-55082A.

The host to be used for the production of the luminescent enzyme of the present invention is not particularly limited and any host generally used for protein production may be used. Examples of the usable host include prokaryotic cells (e.g., *Escherichia coli*), and eukaryotic cells originated from mammals, insects, plants, and the like. The production of the luminescent enzyme may also be performed directly using an organism of an insect, plant, or the like as a host.

Further, the production of the luminescent enzyme may also be performed with a cell-free expression system without using cells.

The vector to be used for the production of the luminescent enzyme is not particularly limited and any vector capable of expression in the host cell may be used. When *Escherichia coli* is used as a host cell, examples of usable vectors include pBluescript, pET21, pTrc99A, pCA24N, pUC18, pUC19, pBR322, pCold, pBad, and the like. A preferred embodiment uses a vector group having a suppressor lacTq, and a PT5-lac promoter inducible by IPTG. Another preferred embodiment uses a vector group having a cold-inducible promoter or an arabinose-inducible promoter.

The introduction of an expression vector to be used for the production of the luminescent enzyme into *Escherichia coli* may be performed using a known method, such as a calcium chloride method, calcium chloride/rubidium chloride method, electropolation method, electroinjection method, a method using a chemical treatment such as PEG, a method using a gene gun or the like, and the like.

The culture of *Escherichia coli* transformed by the expression vector preferably contains a carbon source, inorganic nitrogen source, or an organic nitrogen source required to raise the host cell (transformant). Examples of the carbon source include glucose, dextran, soluble starch, sucrose, methanol, and the like. Examples of the inorganic or organic nitrogen source include ammonium salts, nitrates, amino acids, cornstarch liquor, peptone, casein, meat extract, soybean cake, potato extract and the like. It may optionally include other nutrients (e.g., inorganic salts (e.g., sodium chloride, calcium chloride, sodium dihydrogen phosphate, magnesium chloride), vitamins, antibiotics (e.g., tetracycline, neomycin, ampicillin, kanamycin, or the like), and the like). The culture is performed by a method known in the related fields. The culture conditions, including the temperature, pH of the medium, and the culture time, are suitably selected to enable mass production of the variant luciferase of the present invention.

The luminescent enzyme of the present invention may be obtained as follows from a cultured product obtained by the above culture. More specifically, when the protein of the present invention accumulates in the host cells, the host cells are collected by centrifugation, filtration, or similar operations, and the collected cells are suspended in an appropriate buffer (e.g. Tris buffer, phosphate buffer, HEPES buffer, MES buffer or the like having a concentration of about 10 to 100 mM. Although pH varies depending on each buffer, pH preferably falls within a range of about 5 to 9 (e.g., pH 5.0 to 9.0)) and then disrupted in a manner suitable for the host cell used, followed by centrifugation to obtain the contents of the host cells. In contrast, when the protein of the present invention is secreted outside the host cell, the host cells are separated from the culture medium by centrifugation, filtration, or similar operations, thereby obtaining a culture filtrate. The host cell-disrupted liquid or the culture filtrate may be subjected to purification and separation of the luminescent enzyme of the present invention either directly or after performing ammonium sulfate precipitation and dialysis.

The luminescent enzyme of the present invention may be purified as a fusion enzyme combined with a His tag or a maltose-binding protein using an affinity column containing a metal ion (e.g., when a His-tag is used) such as Ni or Co, or amylose (e.g., when a maltose-binding protein is used). Examples of an affinity column include Ni-Sepharose, amylose-binding gels, and the like.

Elution from the affinity column is preferably performed using imidazole. The concentration of imidazole is generally about 100 to 1000 mM, and preferably about 200 to 300 mM.

Embodiments of the present invention include a nucleic acid (DNA, RNA (in particular, mRNA)) encoding the luminescent enzyme protein and a gene construct having the nucleic acid. The present invention further encompasses the complementary strand of the nucleic acid encoding the luminescent enzyme. Examples of the nucleic acid of the present invention include cDNA. As shown in the Examples described later, the cDNA of the present invention is intron-free, and thus does not naturally occur. The nucleic acid of the present invention may be a single-stranded or double-stranded nucleic acid.

In one preferred embodiment of the gene construct of the present invention, in the gene construct, a nucleic acid encoding the luminescent enzyme (hereinafter, this nucleic acid may be referred to as a "luminescent enzyme gene") and a promoter sequence located upstream of the luminescent enzyme gene are disposed. Preferably, the promoter sequence and the luminescent enzyme gene are connected so that the luminescent enzyme gene can be expressed (in other words, can be operated) based on the activity of the promoter. Examples of the promoter include CMV, R-actin, and like constitutive expression promoters and target gene promoters. Instead of the promoter, a cloning site allowing insertion of a promoter may be disposed. The cloning site may have one or more restriction enzyme cleavage sites.

In one preferred embodiment of the gene construct of the present invention, an element for efficient translation, an mRNA stabilizing element, and the like may be disposed. Examples of the element for efficient translation include a kozak sequence (Ko). Examples of the mRNA stabilizing element include β-globin intron II. Further, for example, a cloning site (e.g., multi-cloning site), an enhancer sequence, IRES sequence, a poly-A addition sequence (e.g., SV40-originated poly-A addition sequence), a drug resistant gene (neomycin resistant gene (Neo$^r$), etc.) selection marker may also be disposed.

The gene construct of the present invention may be a vector (recombinant vector). The vector of the present invention may be obtained, for example, by inserting a luminescent enzyme gene or the above gene construct into an appropriate known vector. In one embodiment, the vector of the present invention includes a non-natural nucleic acid sequence. The vector in this case does not naturally occur. The vector is not particularly limited insofar as it is replicable in a host. Examples of the vector include a plasmid, a shuttle vector, a helper plasmid, and the like. Further, when the vector itself does not have a replicative capacity, a DNA fragment that exhibits a replicative capacity, for example, by being inserted in the host chromosome, may be used.

Examples of the plasmid DNA include *E. coli*-originated plasmids (e.g., pBR322, pBR325, pUC118, pUC119, pUC18, pUC19, pBluescript, etc.), *Bacillus subtilis*-originated plasmids (e.g., pUB110, pTP5, etc.), and yeast-originated plasmids (e.g., YEp plasmids such as TEp13 and YCp plasmids such as YCp50, etc.). Examples of the phage DNA include λ phage and the like. Furthermore, animal viruses, such as a retrovirus or vaccinia virus, and insect virus vectors, such as a baculovirus, may also be used.

Embodiments of the present invention include a cell (preferably a mammalian cell) in which the above gene construct is introduced. Examples of the method for introducing the gene construct into a cell include a calcium phosphate method, DEAE-dextran method, cationic liposome method, and like chemical methods; an adenovirus vector, vaccinia virus vector, retroviral vector, HVJ liposome and like biological methods; and electroporation, DNA direct injection, gene gun, and like physical methods. A suitable introduction method may be selected according to the cell to be introduced.

The gene construct may be present outside the genome of the cell in which the gene construct is introduced (i.e., a transient gene transfection), or may be inserted into the genome of the cell (inserted in the chromosome) by homologous recombination or the like (i.e., a stable gene transfection).

Examples of mammals include humans, cows, horses, sheep, monkeys, pigs, mice, rats, hamsters, guinea pigs, rabbits, dogs and the like, and preferably humans.

The luminescent reaction of the luminescent enzyme of the present invention and the luminescent substrate thereof may be performed according to a method used for previously-known luminescent enzymes.

A preferred embodiment of the present invention provides a luminescent enzyme having a luminescence wavelength of 490 nm to 530 nm at the peak (maximum) intensity. By combining this enzyme with other luminescent enzymes (luciferases) that produce lights separable from each other, a multiple luminescence system can be constituted. The expression "separable from each other" used herein means that the ratios of the luminescent amounts of the individual lights are measurable using, for example, a filter (color filter, bandpass filter, etc.). The measurement of the ratios of the luminescent amounts of the individual lights becomes possible when the difference in maximum luminescence wavelength is, generally, 20 nm or more, preferably 30 nm or more, more preferably 40 nm or more, and particularly preferably 50 nm or more, although it depends on the filter performance or the peak shapes of the respective luminescence spectra. With this degree of difference in maximum luminescence wavelength, for example, by using filters between the respective maximum wavelengths and measuring the transmittance of each luminescence before and after the filter, followed by conversion, it is possible to simultaneously quantify the luminescence amounts of the individual lights.

Examples of other luminescent enzymes (luciferases) to be combined include green to red luciferases originated from the railroad worm (including its variants, the maximum emission wavelength: 535 to 635 nm, for example 540 to 630 nm); orange to green luciferases of *Pynearinus termitilluminans* (including its variants, the maximum emission wavelength: 530 to 600 nm); orange to green luciferases of the *Iriomote* firefly (including its variants, the maximum emission wavelength: 550 to 590 nm); blue luciferases originated from *Cypridina, Renilla, Gaussia, Oplophorus gracilirostris* (including their variants, the maximum emission wavelength: 460 to 490 nm), and the like.

The present invention also provides a kit to be used for bioluminescence. The kit comprises at least one member selected from the group consisting of the above luminescent enzyme proteins, the gene construct (e.g., vector), and a cell. The kit of the present invention may further comprise a luminescent substrate, a culture medium for use in cell culture, a solution for use in cell disruption (buffer), and a solution for use in a luminescent reaction (buffer). The kit may also comprise instructions for bioluminescence.

The kit of the present invention may be produced by equipping the above components as necessary according to a usual method.

EXAMPLES

The present invention is more specifically explained below in reference to Examples. The present invention is, however, not limited to those examples.

Example 1: Luminescent Reaction of Luminescent Enzyme and Luminescent Substrate Crude Liquid Extracts Extracted from Luminescent Lugworm Luminescent lugworm *Odontosyllis undecimdonta* were collected from Toyama Bay, and used after being frozen on dry ice and stored in an ultra-low temperature freezer.

Five individual frozen lugworms were pulverized in 200 µL of a 50-mM acid buffer solution (pH 8.0) by crushing with the tip of a pipette, followed by centrifugation using a superspeed refrigerated microcentrifuge at a relative gravity of 20000 g at 4° C.; then the supernatant was collected and stored overnight in a refrigerator to prepare a luminescent enzyme crude liquid extract. Further, 50 individual frozen lugworms were immersed in 1.5 mL of 99.5% ethanol, followed by centrifugation in the same manner as above; then the supernatant was collected to prepare a luminescent substrate crude liquid extract.

Only 5 µL of the luminescent enzyme crude liquid extract was added to a 50 mM phosphate buffer solution (pH 8.0) containing 100 µL of 300-mM sodium chloride and 20-mM magnesium sulfate, and measurement using a luminometer (CLX-101; Toyobo Co., Ltd.) was performed. The measurement confirmed that the relative luminescent unit (RLU) was kept at around 20 for at least 30 seconds from the beginning of the measurement. 2 µL of the luminescent substrate crude liquid extract was further added to the mixed liquid and rapidly mixed, followed by measurement using a luminometer. As a result, RLU was kept at around 140000 for at least 30 seconds from the beginning of the measurement. Further, the luminescent enzyme crude liquid extract did not have cross-reacting activity with respect to known luminescent substrates such as coelenterazine, *Cypridina* luciferin, or furimazine. The results strongly suggested a possibility that the luminescence of *Odontosyllis undecimdonta* is an LL-type luminescence, and that, further, the structure of the luminescent substrate thereof is different from those of known substrates.

Example 2: Analysis of Luminescent Enzyme Contained in Luminescent Lugworm Luminescent Fluid To carry out the previously-known method for serially obtaining high purity luminescent enzymes through purification using a column or the like, it is necessary to ensure a large amount of primary samples. Thus, the method is not realistic in recent times. Therefore, the present inventors carried out extensive research and found that a protein component in the luminescent fluid secreted by a luminescent lugworm contains a large amount of very high purity luminescent enzyme, thereby obtaining a luminescent enzyme sufficient in amount and quality without a purification process. With this finding, the inventors identified a luminescent enzyme directly from the luminescent fluid itself, as described below.

A luminescent lugworm *Odontosyllis undecimdonta* was lightly stimulated with a fingertip, and only the luminescent fluid was collected. The protein contained in the luminescent fluid was separated by the SDS-PAGE method. After staining it with Coomassie Brilliant Blue, a gel fragment containing about 32 kDa of protein was cut out using a cutter knife and collected. FIG. 1 shows an SDS-PAGE electrophoretogram of a luminescent fluid of luminescent lugworm *Odontosyllis undecimdonta*.

The resulting fragment was added to a buffer, and a luminescent substrate crude liquid extract was added thereto; as a result, luminescence activity was confirmed, thereby confirming that the fragment contained a luminescent enzyme. Another gel fragment was finely cut and 50% acetonitrile was added thereto, followed by shaking to perform decoloring. The decolored fragment was placed in a 100-mM oxyhydrogen ammonium aqueous solution containing 20 mM DTT, followed by a reaction at 56° C. for 30 minutes. Further, a 100-mM ammonium hydrogen carbonate solution was added thereto, followed by shaking for 20 minutes and the solution was discarded. Thereafter, acetonitrile was added and the gel fragment was dehydrated, followed by drying with a vacuum centrifuge. The dried gel fragment was swollen by a 100-mM ammonium hydrogen carbonate solution containing 0.2 µg of trypsin, and left to stand overnight at 37° C., thereby digesting the protein. Further, a 50% acetonitrile solution containing 0.15% trifluoroacetic acid was added, followed by shaking for 20 minutes, thereby extracting peptide. The peptide fragment was desalted using ZipTip C18 (Millipore), and subjected to mass analysis. The mass analysis was performed using ultra TOF/TOF (Bruker Daltonics).

Figure 2:
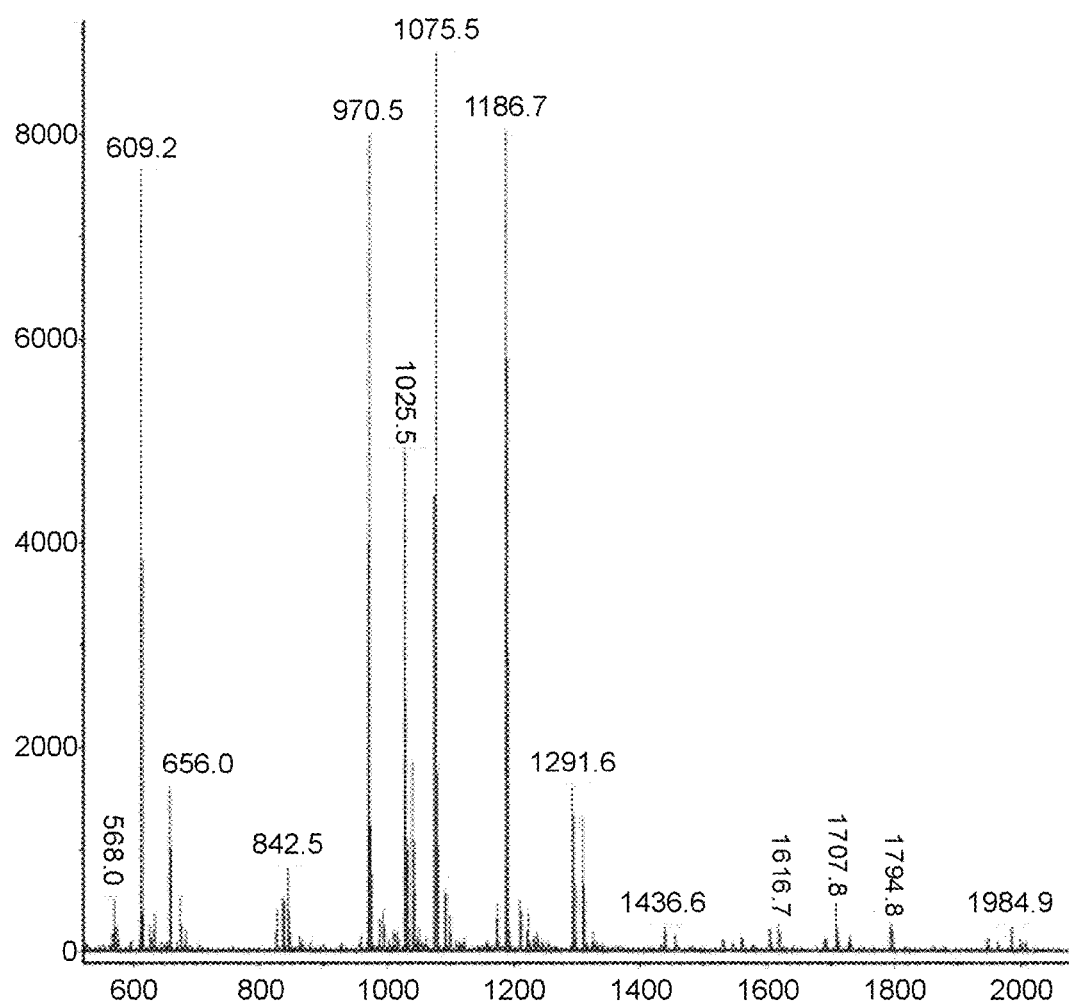
FIG. 2 shows the results of mass analysis.

FIG. 2 shows the analysis results of mass analysis. The measurement mass (m/z) had strong peaks at 970.515 and 1075.493. Further, by performing MS/MS measurement, the presence of a peptide fragment having an amino acid sequence: asparagine-valine-valine-proline-leucine-tryptophan-serine-arginine (NVVPLWSR, SEQ ID NO: 11) and an amino acid sequence: tryptophan-glutamic acid-aspartic acid-tryptophan-valine-asparagine-alanine-arginine (WEDWVNAR, SEQ ID NO: 12) was assumed.

Example 3: Analysis of Luminescent Lugworm-Originated mRNA and Cloning of cDNA

Total RNA was extracted from a frozen sample of luminescent lugworm *Odontosyllis undecimdonta* using Trizol reagent (Thermo Fisher Scientific) according to the product's protocol, and mRNA was collected using a MicroPoly (A) Purist Kit (Thermo Fisher Scientific) according to the product's protocol. Further, a sample library to be subjected to RNA-seq analysis was produced using the NEBNext mRNA Library Prep Master Mix Set for Illumina (NEB) according to the product's protocol. The sample library was subjected to a sequence analysis using MiSeq (Illumina) equipped with MiSeq Reagent Kit v3 (600-cycles). The obtained sequence was analyzed by an NGS analysis platform provided by National Institute of Genetics, thereby finding a nucleic acid sequence represented by SEQ ID NO: 1 potentially encoding a single protein having the peptide fragment sequence obtained in Example 2 and its analogous sequence. This sequence has 1252 bases and an ORF (Open Reading Frame) that encodes a polypeptide having 329 residues shown in SEQ ID NO: 2. The sequence also has 57 bases that are assumed to be 5'UTR, and 205 bases that are assumed to be 3'UTR.

The ORF was subjected to a homology search with respect to a non-redundant database having about 77 million gene sequences using BLAST provided by NCBI, USA; however, the results showed no hits for known luminescent enzymes. Further, no genes with significant homology were found in the conserved domain, and the highest E-value was 2.3, which was the value of predicted: CMRF35-like molecule 4-like of *Astyanax mexicanus*.

Further, using, as a template, an *Odontosyllis undecimdonta*-originated cDNA library prepared using the SMART cDNA Library construction kit (Clontech Laboratories, Inc.), the ORF region in which an NdeI recognition sequence was added to the 5' end and an XbaI recognition sequence was added to the 3' end was amplified by PCR that repeated 30 cycles, each cycle consisting of 98° C. for 10 seconds, 55° C. for 30 seconds, and 72° C. for 1 minute, using primers of SEQ ID NO:3 and SEQ ID NO:4 and ExTaq (Takara Corporation). The resulting DNA fragment was inserted into a pCR4.0-Topo vector (Thermo Fisher Scientific), and a plasmid having the ORF region was obtained.

PCR Primers:
catatgaagt tagcactgtt actcagc (SEQ ID NO: 3)
tctagactgt tgtaggttat acatctcagc (SEQ ID NO: 4)

Example 4: Analysis of Genomic Region Encoding Luminescent Lugworm Luminescent Enzyme Purification of genomic DNA from a frozen sample of luminescent lugworm *Odontosyllis undecimdonta* was performed using DNeasy Plant mini Kit (Qiagen) according to the product's protocol. Using the obtained genomic DNA as a template, a region encoding cDNA of Example 3 present in the genomic DNA of the organism was amplified by PCR that repeated 30 cycles, each cycle consisting of 98° C. for 10 seconds, 55° C. for 30 seconds, and 72° C. for 6 minutes, using primers of SEQ ID NO: 3 and SEQ ID NO: 4 and ExTaq (Takara Corporation). The resulting DNA fragment was inserted into a pCR4.0-Topo vector (Thermo Fisher Scientific), and a plasmid having the genomic region was obtained. The base sequence analysis of the plasmid was performed. The results of the analysis of the whole length revealed that, on the genome, the cDNA is coded as 8 operons in the genomic DNA of 4804 bases shown in SEQ ID NO: 5.

Figure 3:
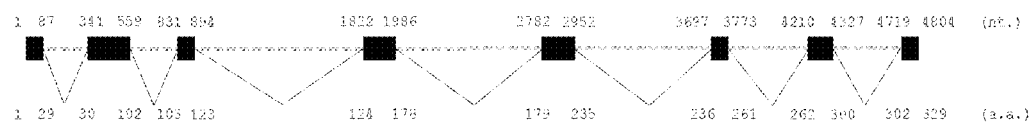
FIG. 3 is a schematic view of an operon structure encoded on the genome. The numbers in the upper and lower rows denote the numbers of nucleotides and amino acids, respectively.

FIG. 3 is a schematic view of the operon structure. Tables 1 to 4 show the correspondence relation between the genome sequence of SEQ ID NO: 5 and the amino acid sequence of SEQ ID NO: 2 encoded by the operon region. Leu encoded by TTA is considered to exist across the 7th operon and the 8th operon. Table 1 shows three amino acid sequences, which are represented by SEQ ID NO: 13, SEQ ID NO: 14, and SEQ ID NO: 15, respectively. Table 2 shows one amino acid sequence, which is represented by SEQ ID NO: 16. Table 3 shows two amino acid sequences, which are represented by SEQ ID NO: 17 and SEQ ID NO: 18, respectively. Table 4 shows two amino acid sequences, which are represented by SEQ ID NO: 19 and SEQ ID NO: 20, respectively. The combination of the amino acid sequences, in consecutive order, represented by SEQ ID NOs: 13-20 provide the amino acid sequence represented by SEQ ID NO: 2.

TABLE 1

| | |
|---|---:|
| ATG AAG TTA GCA CTG TTA CTC AGC ATT GGA TGT TGC CTG GTT GCC GTC<br>Met Lys Leu Ala Leu Leu Leu Ser Ile Gly Cys Cys Leu Val Ala Val | 48 |
| AAC TTT GCT TTA AGG GCT ACT ATC ATA AGA TGT CTT AGG GTA AGA CTT<br>Asn Phe Ala Leu Arg Ala Thr Ile Ile Arg Cys Leu Arg Val Arg Leu | 96 |
| CAG AAA CTC ATA TTG ACC ATG AGG GCC TCT ATA ATA ATA TTT CTT AAT | 144 |
| GTA AGA CTA CAG AAG CTC ATA TTG ACC TTA AGG GTC TCT ATA ATA ATA | 192 |
| TTT CTT AAT GTA AGA CTA CAG AAG CTC ATA TTG ACC TTG AGT CTC TAT | 240 |
| AAT AAT ATT TCT AAA TGT AAG ACA ACA GAA GCT CAT ATT GAC CTT GAG | 288 |
| GGT CTC TAT AAT AAT ACA TAT AAT TAC ATC TTG ATT AAA TTA TTT CTC | 336 |
| TTAG AAA ACT AGA AGT TGG TCA GAA ATA GAT TGT ACA CCA CAT CAG GAC<br>    Lys Thr Arg Ser Trp Ser Glu Ile Asp Cys Thr Pro His Gln Asp | 384 |
| AAG CTA TAT GAG GAC TTT GAC AGG ATC TGG GCT GGA GAT TAC CTG TCA<br>Lys Leu Tyr Glu Asp Phe Asp Arg Ile Trp Ala Gly Asp Tyr Leu Ser | 432 |
| GTA TTT GCC GAA TGG TTA GAT AAT CCC ATC CCT CGA GAG TGG TCT GAG<br>Val Phe Ala Glu Trp Leu Asp Asn Pro Ile Pro Arg Glu Trp Ser Glu | 480 |
| GAA AGA CTG GCC ACA TAC TGC ATA GAG AGG GAA TGT CAC ACT AAT CAA<br>Glu Arg Leu Ala Thr Tyr Cys Ile Glu Arg Glu Cys His Thr Asn Gln | 528 |
| GCT ATG GTG GAC TAT ATG AAT ATA CAT GGG GT AAA GTT TTA GCA CAT<br>Ala Met Val Asp Tyr Met Asn Ile His Gly | 576 |
| GTT TTT ATG TAC AGT ATC TGC TTT ATT ATG GTT TTA ATC GTA GTA CAT | 624 |
| TTT ATA TGT ATA GTA TCT GCT TTA TTA TGG TTT TAA TCT TAG TAC ATG | 672 |
| TTT ATA TTT ACA GTA TGC CCC TTA TAA TGG TTT TAA TCT TGG TAC ATG | 720 |
| TTT GTA CTT ACA GTA TCT GCT TTA TTA TGG TTT TAA TCT TAG TAC ATG | 768 |
| TTT GTA TTT ACA GTA TCT GCC TTA TTA TGG TTT TAA TCT TAG TAC ATG | 816 |
| TTT TGT ACT TAC AG TAT GCC CCT TTT TGC ATG GAA AGG AGT GTT GAA<br>    Tyr Ala Pro Phe Cys Met Glu Arg Ser Val Glu | 864 |
| GAC TGG GTG AAT GCT AGA TTC TGG ACT AGG TATG CAG TTT CAT CAA ATG<br>Asp Trp Val Asn Ala Arg Phe Trp Thr Arg | 912 |
| TTT ATA TCA ATA AAA TAT AAT GCT TAG TAA AGC AGC TGC CAA TCC GGG | 960 |
| TTA AGT ATT TTT TTT CCA AGC ACA TTT GTA CAA AAC GGC ATA GTA TCC | 1008 |
| ATA GTG TAG GGA CAA TTC TTT GGA ATG GTC AAT TCT ACA CTG CAG TCA | 1056 |
| GTG ATT GAT AGT TAT AAA TAT GTC AGA TTC AGC AAT TAA TGG TTA ATG | 1104 |
| AAT GAA TTG CTA TTT ACC ACA ATG TTG TAC CAT TAC AAC ATT CAG CTA | 1152 |
| GGC TGT CCA GCC ATC AAA CAC ATA CTC AGT GTG CTC CTT CTA CAT ATT | 1200 |
| TGT ACT GAT CTG CAC TAC ATG GAA GTT TTT TCT AGA CTA GTG GTG CAT | 1248 |

TABLE 2

| | |
|---|---:|
| GTA TTG CAT ATG ACT GTA CTT TAG TTC TAG GAA AGG AGA GTG TTA ACT | 1296 |
| ACA CCC TTG AGT AGT TAT AGG CAA CAA ACA TGA AGT TAC CTT TTC AAT | 1344 |
| TGA ACC ATG TTG ACA GTG GGC TGT ATA CAG CTC GGA AGT AGC CTA AGC | 1392 |
| AGG GTA AAA GTA GCC AAT AAA TCA TAT TGT GGC AAA CAG CAA TTC CTT | 1440 |
| TTG CCT CAT AAA TAA TTA ATG ATG GAT ATT CCA AAA GTG TCT AGG GG | 1488 |
| AGA GTG AGA GAC TTT TTT GAA GAA ATT GTA TGG TTT TAG ATA ACA GTC | 1536 |
| ATA CTA TAT ACA AAT AGT TGC AGC CAA ATC TCT TCC TTT CTT CAA GAT | 1584 |

TABLE 2-continued

```
AAT TTG TTT CTT CAT CAT TTA CTA CAT TCC CAA ATT GTT CTG TGG CAA      1632

GTT GAA AAT AGG AAA AAC ATC CTA CAA ATT GGA TTC TGA TTC CTC ATA      1680

ACC TAA GGC AAA CTC ATC TCC TTG ATT CAG AAT GTA GCA ATA ATC TAC      1728

CCA TAT TAC CCA TGT AAT TTG TTT CAT TGA CCT TCA AAT CAA ATG CTC      1776

TGT TAT TCC TCC TCA TTA TCA ATA ATA TGA TTA CTT TTG CAG A TGT        1824
                                                              Cys

AAG GTT AGA ACT GAT CGT AGT TTA GAA CTG GCA CCT GAA GAA TAT GCC      1872
Lys Val Arg Thr Asp Arg Ser Leu Glu Leu Ala Pro Glu Glu Tyr Ala

ACC TAC TTT TGT TAT AAG GTG TTT CGT GTA CAG GAT CCT AAA ATA GCT      1920
Thr Tyr Phe Cys Tyr Lys Val Phe Arg Val Gln Asp Pro Lys Ile Ala

TGT CCC TCG ATG GAT GTG ATC CTT TCA CCT AAC AAA CTG ACT GTA CAA      1968
Cys Pro Ser Met Asp Val Ile Leu Ser Pro Asn Lys Leu Thr Val Gln

CAA ATG ATG CAA AAT AAG GT AAG AAC CAC CCC TAA GCC AGG CCA TAC TTA   2016
Gln Met Met Gln Asn Lys

TTT GAT AGT TCA GAC TCA TGT GCA GGA AGG AGT GCC CTG TGA CAT ACT      2064

GCA TAT ATT TTG AAC CAA AAT ATT TGT ATA CTT GTA GTT AAA ATC AAT      2112

GTG AGC GAG ACT TTA GAT AAG AGC CAA TGG TTC ATT AGA TAG TCC AAA      2160

TCA ATG TGA GCG AGA CTT AGA AGA GCC AAT GGT TCG GTA GAT AGT          2208

CCA AAT CAA TCT GAG CTA GAC TTT AGA GAA GAG CAA TGG TTC ATT AGA      2256

TAG TTC AAA TCA ATA TGA GCT AGA CTT AGA AGA GCC AAT GGT TCG          2304

GTA GAT AGT CCA AAT CAA TCT GCG CTA GAC TTT AGA GAA GAG CAA TGG      2352

TTC ATT AGA TAG TCC AAA TCA ATA TGT TTC TAG ACT TTA GAG AAG AGC      2400

CAA TGG TTC ATT AGA TAG TTC AAA TCA ATA TGA GCT AGA CTT TAG AGA      2448

AGA GCC AAT GGT TCA TTA GAT AGT TCA AAT CAA TAT GAG CTA GAC TTT      2496

AGA GAA GAG CAA TGG TTC AGT AGA TAG TTC AAA TCA ATA TGA GCT AGA      2544

CTT TAG AGA AGA GCC AAT ACA ATA TGA GCT AGA CTT TAG AGA AGG CCA      2592

AGT GGT ATA AGG TGC AAT TAA TCT CAA TAA AAG AGT CAA ACC TTT GAG      2640

AAG ATA GCT TGA ATC TTA AGA AGG AAG GCA TCT AAA TAG AAG ATC CAC      2688
```

TABLE 3

```
AAG ATT GTT TAA ATT AAG GGA GAC ACA GCT AAA CGA AAA AGC CAA GAA      2736

GGC TAA TGA AGC GGT ACT GAC ATT TTT ACT TGT TTA TAC CAC AG GAA       2784
                                                               Glu

ATA AGA GGA GTT GTA GAG GAT AGA TCT GAG CAA TGG TGG GTT GGA CTA      2832
Ile Arg Gly Val Val Glu Asn Arg Ser Glu Gln Trp Trp Val Gly Leu

ATG AGA GAA ATA TCG CAT CTG TCT AAG GAC TTG AAT GGT GTG AAA CAA      2880
Met Arg Glu Ile Ser His Leu Ser Lys Asp Leu Asn Gly Val Lys Gln

TTC CAT TAT GGA TGG ATC ATA AAC ACA GCT ACA CAA AAG AAT GTG GTT      2928
Phe His Tyr Gly Trp Ile Ile Asn Thr Ala Thr Gln Lys Asn Val Val

CCT TTG TGG TCA CGT TAT CAG GGG GTAA GAA ATT CTA CAT TAT AAG AAT     2976
Pro Leu Trp Ser Arg Tyr Gln Gly

GTG ATT TAT TAA GCT TGC TCA TCA CTT TGT GTT GGC ACA TTG TAT TTG      3024

CTA CTG CTA GAT CCT TGA GTG AAC TTA ACT CAT ATA ACT TAG AAT CTG      3072

CAT GCA TAT TTT CAA CTA GAC ATA GTA ATA ATA TTT TAC ATA AAT CAC      3120

TTC CTT GCA TAA CAG AAA ATG TTC TGA ATT TGT ATT AAA ACA GTC CTT      3168
```

TABLE 3-continued

```
AAC TCT GGA CCC TCT AAA CAT TAA AAA TAC TGT TGG ACC CTA AGT CCA    3216

TTT TAA AGT GAG CTA AGT CAA GTC CCA CTG TTA TAG CAA TTT TAA ATT    3264

TAA ATG AAG CCT CCA GTC AAG ATT GCA AAA AGT CTC AGA AGG ATA CAG    3312

ATT TGT GAT CCC CCT CTA AAA TTT GTA AAT AAC AAA ATG AAT AGA TCT    3360

TGA CAT AGC CAT ACA TAT TTG CAT ATG ACT ATC CAA AGG TTT TTG GAG    3408

AGA GAT AAT TTT TCT CCT CCC ATT AGG AGG TGT TTT TGA GGT AAC CAA    3456

AAT ATT ACC CCC CCT CCC CAT GGA TAT GGA TGA GGG GTA TAC TTT TCT    3504

TTC ATA TTT CAA TCT AAA AAT CCC TTT TCA CAA CTT AAA CAA TTT GAA    3552

CTT AGT TTA CAC TAA GTC AAC TAA TTT AGT ATC CCA TCC TTT TAC CTA    3600

CTT GTA GTC TGA AAC TGT GTG GTA TTA GGA AGA ATC ACA GTT TAA ATG    3648

TAC ATG AGC TAT TTT AGC CCA ATA CAA ACT AAT GAT ATT TTT TTC AGC    3696

CCT ACT ATT CCA GTA AGA AGA GAC ATG CCT AGA ATC ATT AAT GCC ATG    3744
Pro Thr Ile Pro Val Arg Arg Asp Met Pro Arg Ile Ile Asn Ala Met

TCT AAT GGA GGA GGA AAC ATT ACC TTG GGA GGTA AAT AAA TAA ATA AAA  3792
Ser Asn Gly Gly Gly Asn Ile Thr Leu Gly

ACT TGT ATA AAC ATA AAT ATT GCA TCA CTG AAG CAA ATA AAC CTA TCT    3840

ACC TGC TGA AGC TGC TAA ACT GGA TAT TCA CTG AAC ATT TGT AAT ATT    3838

TGG TTT ATT ATT ATG TTG ATG GGA TTC AAA TAA TAA TAA AAT TTA CAA    3936

ATA TAT GTT CTG TAA AAT TGG CAG CCA GCC AGG AAA AAC GAT AAA ATA    3984

TAG ATG TAT ATT GTA TTG TTG TCA CTT TTT ATC CAA TTT AGA GAC CAG    4032
```

TABLE 4

```
GAT GAA ACA TTT AGT CAA TAA TAA ACA TAT ATA TAT AGT TAT TTT ATT    4080

AAA TCT CAA GCT ACA ATT ATA AGT GCT GGT AAA TAG TTG ATC AAT AAC    4128

CAT TTT TCA TGA AAT AAA TAA AAT AAA ATG ATC ACT AAA ATC TCA ATA    4176

CAT CAT CAT AAC TAC AGA TAA ATT ATT TTG TA GAT ATT CGA AAT TTC    4224
                                          Asp Ile Arg Asn Phe

CAC TGC TCT CCT GAT CCA GAC AGT GTT GCT GTC ATC TGC CCT GAG TTC    4272
His Cys Ser Pro Asp Pro Asp Ser Val Ala Val Ile Cys Pro Glu Phe

GGT TTC TTG TCC TAT AGC CCA GCT GAA ACT ATA GTA ATG GTT CCA GTA    4320
Gly Phe Leu Ser Tyr Ser Pro Ala Glu Thr Ile Val Met Val Pro Val

AAT GGA__T__ GTA AGA TTG CAT TTC CTT ATT ATC TAA ATA ATA ATT ATG TAG  4368
Asn Gly

AGT ACT ACT TCC CCC TTC AAG CTG TTT ATC CAG TCT TTG TTA TCT CAT    4416

ATT CAA TAT TCT GTG TAA TAA GTT TAA CCC TCA AGA ATA GAA ATG TAA    4464

GCC TGC AGG TGT AGT AAT GAC CTC CTG TAG GTG TAG TAA TGG CCT CCT    4512

GTA ACC AGT AGT ATT AAT CGT ATA AAG TAT ACT ATT CTC ATT ACA ACA    4560

CAT CTA GAA CTG TGG AGG CCA AAA GTG GAA ATT GTA AAA CCA TCC ACA    4608

ATA AAC TGG TGC TAT ATA AAA ACG TAG ACT AAG GGA TGT ACA ATT CTT    4656

AAA GTA TCA AAC AAT GAC ACC AAC ACA CCA TCA CTA TTG CCA TAA CTA    4704

TAT TTC TAT TTC AG__TA__ ATC CTG ATG GGA ATG ACA CAA TCT ACA GAT      4752
                    Ile Leu Met Gly Met Thr Gln Ser Thr Asp
```

TABLE 4-continued

```
GGA GTA CCT TTC GTA AAA TCT GCC CTA TTT GCT GAG ATG TAT AAC CTA    4800
Gly Val Pro Phe Val Lys Ser Ala Leu Phe Ala Glu Met Tyr Asn Leu

CAA CAG                                                            4804
Gln Gln
```

Example 5: Construction of Vector for Mammalian Cells

Using the plasmid obtained in Example 3 as a template, after a treatment using primers of SEQ ID NO: 6 and SEQ ID NO: 7 and KOD plus neo (Toyobo Co., Ltd.) at 94° C. for 2 minutes, a DNA fragment of approximately 1000 base length in which HindIII recognition sequence was added to the 5' end and an SmaI recognition sequence was added to the 3' end was obtained by PCR that repeated 30 cycles, each cycle consisting of 98° C. for 10 seconds and 68° C. for 30 seconds. The obtained fragment was treated with HindIII and SmaI (both manufactured by Takara Corporation), and a band of approximately 1000 base lengths was excised by agarose gel electrophoresis from the gel and purified. On the other hand, a treatment with HindIII and SmaI (both manufactured by Takara Corporation) was performed using, as a mammalian cell expression vector, pFLAG-CMV-2 (Sigma-Aldrich), and a band of approximately 4700 base lengths was excised by agarose gel electrophoresis and purified. The resulting insertion fragment and the vector fragment were subjected to ligation using Takara DNA ligation kit <Mighty Mix>, thereby obtaining an expression plasmid pFLAG-GoLuc (GoLuc is identified by SEQ ID NO: 2). Further, in order to produce a plasmid in which the FLAG sequence is removed from this plasmid, after a treatment using primers of SEQ ID NO: 8 and SEQ ID NO: 9 and KOD plus neo (Toyobo Co., Ltd.) at 94° C. for 2 minutes, a DNA fragment of approximately 5700 base lengths was obtained by inverse PCR that repeated 30 cycles, each cycle consisting of 98° C. for 10 seconds and 68° C. for 3 minutes. The 5' end of the resulting fragment was phosphorylated using T4 Polynucleotide kinase (Toyobo Co., Ltd.), and then was subjected to ligation using a DNA ligation kit <Mighty Mix>, thereby obtaining an expression plasmid pΔFLAG-GoLuc.

PCR Primers:

```
                                         (SEQ ID NO: 6)
        acaagcttat gaagttagca ctgttactc (SEQ ID NO: 7)
        aacccgggtt actgttgtag gttatacat (SEQ ID NO: 8)
        atgaagttag cactgttact c (SEQ ID NO: 9)
        ggtagatcaa ttctgacggt t
```

Example 6: Production of Luminescent Lugworm Recombinant Luminescent Enzyme Using Mammalian Cells and Measurement of its Activity Luminescent activity of a luminescent lugworm recombinant luminescent enzyme produced by using mammalian cells was evaluated.

Mammalian cells COS-1 were seeded in a 6-well plate in an amount of $2.5 \times 10^5$ cells/per well, and cultured in an incubator at 37° C., 5 $CO_2$. When the cells were grown to 80 confluent, the expression plasmids pFLAG-GoLuc and pAFLAG-GoLuc produced in Example 5 were introduced into COS-1 for transduction in an amount of 4 μg each, using Lipofectamine (registered trademark) 3000 (Thermo Fisher Scientific). 24 hours after the transduction, the cells were washed with PBS, and 2 mL of serum-free Dulbecco's Modified Eagle Medium (EDEM) was added, followed by cell culture in an incubator for 20 hours. The culture supernatant was collected, and 1 μL of a luminescent substrate crude liquid extract was added to a mixed liquid obtained by adding NaCl and $MgCl_2$ to 100 μL of the supernatant at the final concentrations of 230 mM and 15 mM, respectively, followed by measurement of summed luminescence activity value for 30 minutes. The activity measurement was performed using Luminescencer-Octa AB-2270 (ATTO). The cells were washed with serum-free DMEM, and 10 mM Tris buffer was added, followed by ultrasonic disruption. The disruption fluid was centrifuged, the supernatant was collected, and the activity in 100 μL of the supernatant was measured.

Figure 4:
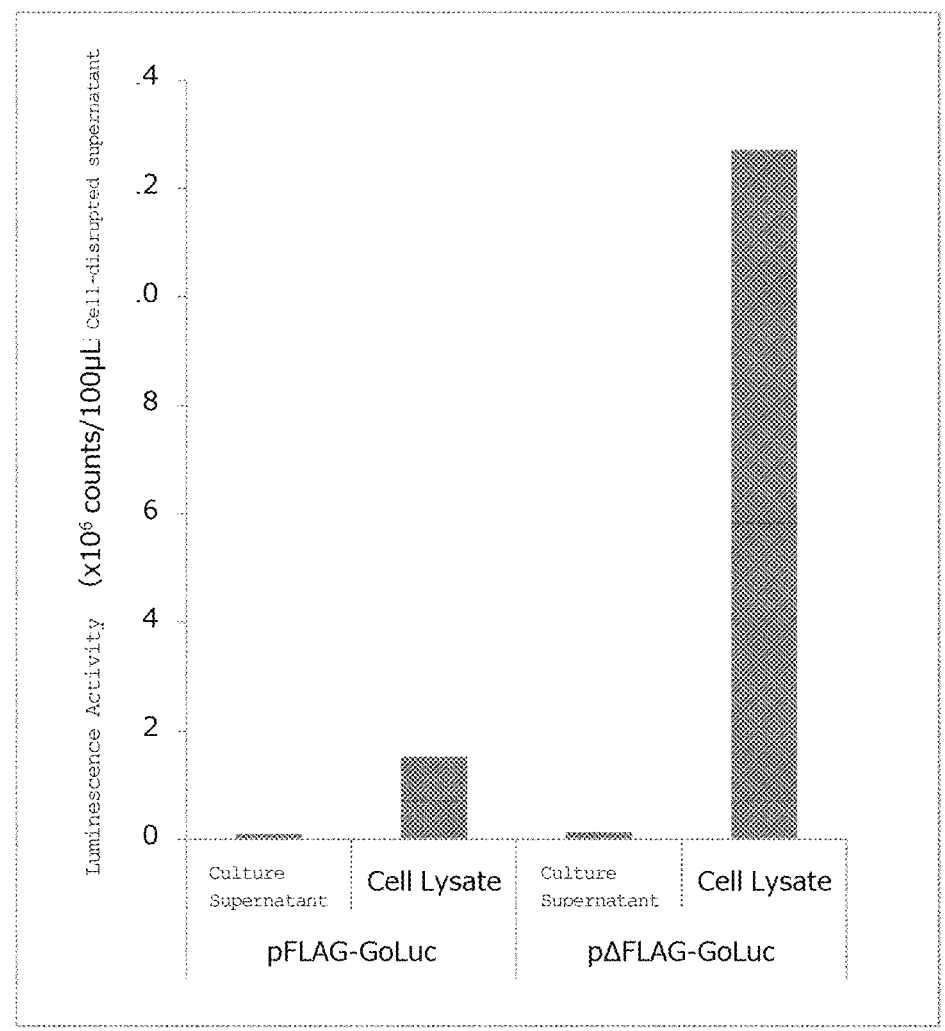
FIG. 4 shows the measurement results with respect to activity in a culture supernatant and a cell lysate (cell-disruption liquid) of a recombinant luminescent enzyme.

FIG. 4 shows the results. The luminescence activity confirmed in the culture supernatant was only about 1%, thus showing that most of the produced luminescent enzyme was accumulated in the cells. Further, the luminescence activity in the cells in which a FLAG-tag expression vector was introduced was about ⅛ of the tagless expression vector.

Example 7: Measurement of Luminescence Spectrum of Luminescent Lugworm Recombinant Luminescent Enzyme 1 μL of a luminescent substrate crude liquid extract was added to a mixed liquid obtained by adding 1 μL of a luminescent substrate crude liquid extract, NaCl and $MgCl_2$, to 30 μL of 10 mM Tris buffer at the final concentrations of 230 mM and 15 mM, respectively.

The luminescence spectrum was measured using an ATTO AB1850 spectrophotometer. The measurement was performed for 30 seconds.

Figure 5:
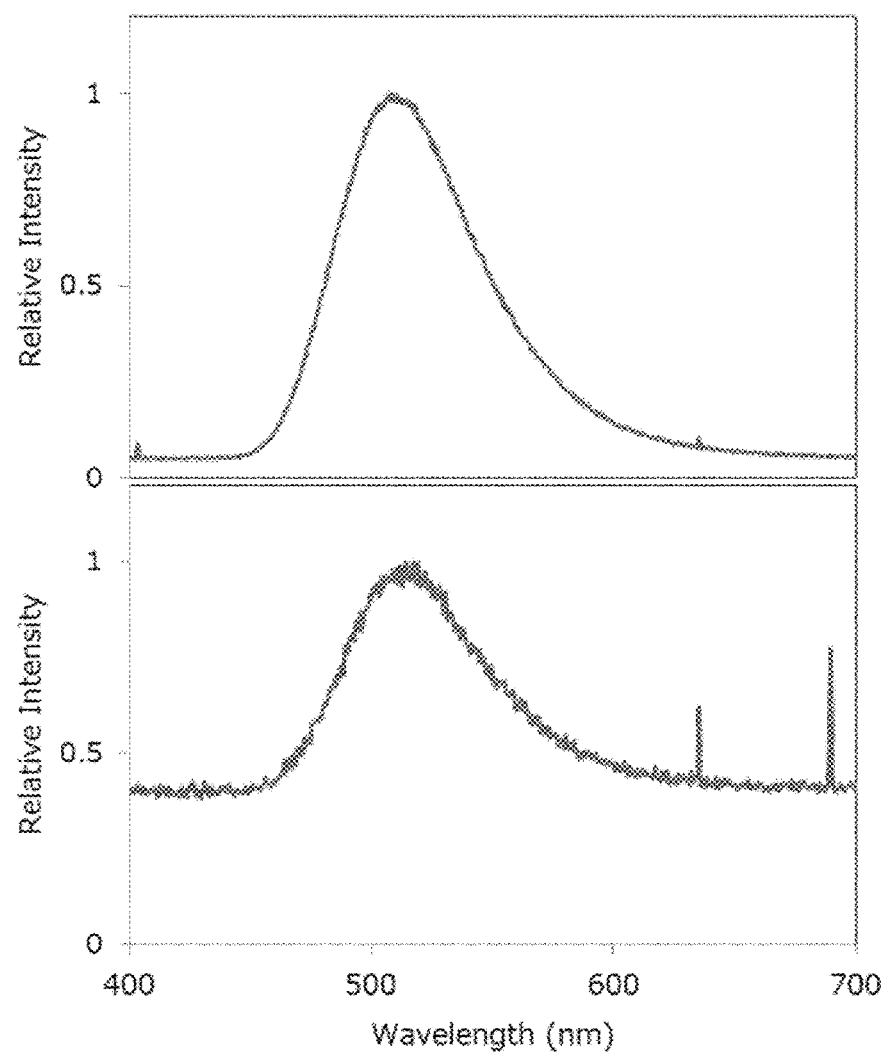
FIG. 5 shows the measurement results of a luminescence spectrum of a recombinant luminescent enzyme.

The upper diagram in FIG. 5 shows the results. As shown in the upper diagram in FIG. 5, a spectrum with the maximum luminescence was observed near 510 nm.

Further, after the transduction of pAFLAG-GoLuc into COS-1 cells, NaCl, $MgCl_2$, and a luminescent substrate crude liquid extract were added to 30 μL of a cell disruption supernatant prepared in the same manner as in Example 6, followed by measurement.

The lower diagram in FIG. 5 shows the results. A spectrum with the maximum luminescence was observed near 510 nm, similar to the case with the luminescent enzyme crude liquid extract. The luminescent enzyme extracted from a luminescent lugworm and the recombinant luminescent enzyme produced from animal cells had substantially the same spectrum.

TABLE 5

[SEQ ID NO: 1]
```
tgagtaacag tgctaacttc atcatcacaa gaagatactt ctcagcttgt attgaagatg    60
aagttagcac tgttactcag cattggatgt tgcctggttg ccgtgaactt tgctttaagg   120
gctactatca taagatgtct taggaaaact agaagttggt cagaaataga ttgtacacca   180
catcaggaca agctatatga agactttgac aggatctggg caggagatta cctgtcggta   240
tttgctgaat ggttagataa tcccatccct cgagagtggt ctgaggaaag actggccaca   300
tactgcatag agagggaatg tcacactaat caagctatgg ttgactatat gaatatacat   360
gggtatgccc cttttttgcat ggaaaggagt gttgaagact gggtgaatgc tagattctgg   420
actagatgta aggttagaac tgaccgtagt ttagaactgg cacctgaaga atatgccacc   480
tacttttgtt ataaggtgtt tcgtgtacag gatcctaaaa tagcttgtcc ctcgatggga   540
gtgatccttt cacctaacaa actgactgta caacaaatga tgcagaataa ggaaataaga   600
ggagttgtag aggatagatc tgagcaatgg tgggttggac taatgagaga aatatcgcat   660
ctgtctaagg acttgaatgg tgtgaaacaa ttccattatg gtggatcat aaacacagct   720
acacaaaaga atgtggttcc tttgtggtca cgttatcagg gcctactat tccagtaaga   780
agagacatgc ctagaatcat taatgccatg tctaatggag gaggaaacat cacccttggga   840
gatattcgaa atttccactg ctcagctgat ccagacagtt tgctgtcat ctgccctgag   900
tttggtttct tgtcctatag tccagctgaa actatagtta tggttccagt aaatggatta   960
atcctgatgg gaatgacaca atctgcagat ggagtaccct tcgtaaaatc tgcactttt  1020
gctgagatgt ataacctaca acagtaagag atcatccagg acactgaggc tgaatgtggt  1080
cattatttat acacagtta ttccctttaat cttttgcaaca ttataattta gttttgataa  1140
tcatgatgat taataagat ataaatataaa catatattat atgatcagat actcttacta  1200
ttcttttat gctttgtttt tttattaaat tatccgcatt ttctattctg at           1252
```

[SEQ ID NO: 2]
```
MKLALLISIG CCLVAVNFAL RATIIRCLRK TRSWSEIDCT PHQDKLYEDF DRIWAGDYLS    60
VFAEWLDNPI PREWSEERLA TYCIERECHT NQAMVDYMNI HGYAPFCMER SVEDWVNARF   120
WTRCKVRTDR SLELAPEEYA TYFCYKVFRV QDPKIACPSM DVILSPNKLT VQQMMQNKEI   180
RGVVEDRSEQ WWVGLMREIS HLSKDLNGVK QFHYGWIINT ATQKNVVPLW SRYQGPTIPV   240
RRDMPRIINA MSNGGGNITL GDIRNFHCSP DPDSVAVICP EFGFLSYSPA ETIVMVPVNG   300
LILMGMTQST DGVPFVKSAL FAEMYNLQQ                                    329
```

[SEQ ID NO: 10]
```
atgaagttag cactgttact cagcattgga tgttgcctgg ttgccgtcaa ctttgcttta    60
agggctacta tcataagatg tcttaggaaa actagaagtt ggtcagaaat agattgtaca   120
ccacatcagg acaagctata tgaggacttt gacaggatct gggctggaga ttacctgtca   180
gtatttgccg aatggttaga taatcccatc cctcgagagt ggtctgagga aagactggcc   240
acatactgca tagagaggga atgtcacact aatcaagcta tggtggacta tatgaatata   300
catgggtatg ccccttttttg catggaaagg tgttgaaga ctgggtgaa tgctagattc   360
tggactaggt gtaaggttag aactgatcgt agtttagaac tggcacctga agaatatgcc   420
acctactttt gttataaggt gtttcgtgta caggatccta aaatagcttg tccctcgatg   480
gatgtgatcc tttcacctaa caaactgact gtacaacaaa tgatgcaaaa taaggaaata   540
agaggagttg tagaggatag atctgagcaa tggtgggttg gactaatgag agaaatatcg   600
catctgtcta aggacttgaa tggtgtgaaa caattccatt atggatggat cataaacaca   660
gctacacaaa agaatgtggt tcctttgtgg tcacgttatc aggggcctac tattccagta   720
agaagagaca tgcctagaat cattaatgcc atgtctaatg gaggagaaa cattaccttg   780
ggagatattc gaaatttcca ctgctctcct gatccagaca gtgttgctgt catctgccct   840
gagttcggtt tcttgtccta tagcccagct gaaactatag taatggttcc agtaaatgga   900
ttaatcctga tgggaatgac acaatctgca gatggagtac tttcgtaaa atctgcccta   960
tttgctgaga tgtataacct acaacag                                      987
```

The invention claimed is:

1. A recombinant vector comprising a nucleic acid encoding the luminescent enzyme protein of:
   (i) a luminescent enzyme protein comprising the amino acid sequence represented by SEQ ID NO: 2;
   (ii) a luminescent enzyme protein comprising an amino acid sequence represented by SEQ ID NO: 2 in which 1 to 32 amino acid residues are substituted, added, or deleted, and having luciferase activity; or
   (iii) a luminescent enzyme protein comprising an amino acid sequence encoded by the base sequence represented by SEQ ID NO: 10 and having luciferase activity;
   wherein the recombinant vector comprises a non-natural nucleic acid sequence.

2. A cell in which the recombinant vector according to claim 1 is introduced.

3. The recombinant vector comprising a nucleic acid encoding the luminescent enzyme protein according to claim 1, wherein the luminescent enzyme protein has a luminescence wavelength of 490 to 530 nm at peak intensity.

4. A cell in which the vector according to claim 3 is introduced.

5. The recombinant vector comprising a nucleic acid encoding the luminescent enzyme protein according to claim 1, wherein the luminescent enzyme protein comprises the amino acid sequence represented by SEQ ID NO: 2.

6. The recombinant vector comprising a nucleic acid encoding the luminescent enzyme protein according to claim 1, wherein the luminescent enzyme protein comprises the amino acid sequence represented by SEQ ID NO: 2 in which 1 to 32 amino acid residues are substituted, added, or deleted, and having luciferase activity.

7. The recombinant vector comprising a nucleic acid encoding the luminescent enzyme protein according to claim 1, wherein the luminescent enzyme protein comprises an amino acid sequence encoded by the base sequence represented by SEQ ID NO: 10 and having luciferase activity.

8. The recombinant vector comprising a nucleic acid encoding the luminescent enzyme protein according to claim 1, wherein the luminescent enzyme protein comprises an amino acid sequence encoded by the base sequence represented by SEQ ID NO: 10 in which 1 to 98 bases are substituted, added, or deleted, and having luciferase activity.

* * * * *